ized Patent US 10,634,668 B2
(12) United States Patent
Espinosa et al.

(10) Patent No.: US 10,634,668 B2
(45) Date of Patent: Apr. 28, 2020

(54) MODIFIABLE CHEMICAL INDUCERS OF PROXIMITY AND METHODS OF USING THE SAME

(71) Applicant: Clontech Laboratories, Inc., Mountain View, CA (US)

(72) Inventors: Eric Espinosa, Mountain View, CA (US); Andrew Farmer, Mountain View, CA (US)

(73) Assignee: TAKARA BIO USA, INC., Mountain View, CA (US)

(*) Notice: Subject to any disclaimer, the term of this patent is extended or adjusted under 35 U.S.C. 154(b) by 242 days.

(21) Appl. No.: 14/023,362

(22) Filed: Sep. 10, 2013

(65) Prior Publication Data

US 2014/0080137 A1 Mar. 20, 2014

Related U.S. Application Data

(60) Provisional application No. 61/700,683, filed on Sep. 13, 2012.

(51) Int. Cl.
*C12Q 1/68* (2018.01)
*G01N 33/53* (2006.01)
*G01N 33/542* (2006.01)

(52) U.S. Cl.
CPC ....... *G01N 33/5306* (2013.01); *G01N 33/542* (2013.01)

(58) Field of Classification Search
CPC .................................. G01N 33/53; C12Q 1/68
See application file for complete search history.

(56) References Cited

U.S. PATENT DOCUMENTS

| 5,866,334 A | 2/1999 | Beutel |
| 5,871,753 A | 2/1999 | Crabtree et al. |
| 7,067,526 B1* | 6/2006 | Yang .................. C07D 498/18 514/291 |
| 9,593,356 B2 | 3/2017 | Haugwitz et al. |

(Continued)

FOREIGN PATENT DOCUMENTS

| WO | 1994018317 | 8/1994 |
| WO | WO-9418317 A1 * | 8/1994 |

(Continued)

OTHER PUBLICATIONS

Rollins et al., "A ligand-reversible dimerization system for controlling protein-protein interactions," PNAS, 2000, vol. 97, No. 13, see p. 7096-7101.*

(Continued)

*Primary Examiner* — Tracy Vivlemore
*Assistant Examiner* — Nam P Nguyen
(74) *Attorney, Agent, or Firm* — Bret E. Field; Bozicevic, Field & Francis LLP

(57) ABSTRACT

Methods of reversibly inducing proximity of first and second target molecules in a sample are provided. Aspects of the methods include contacting the sample with a modifiable chemical inducer of proximity (MCIP) that reversibly induces proximity of the first and second target molecules, upon application of a stimulus that modifies the MCIP. Aspects of the invention further include methods for regulating a biological process in a cell. Aspects of the invention further include compositions, e.g., compounds and kits, etc., that find use in methods of the invention.

18 Claims, 5 Drawing Sheets

(56) References Cited

U.S. PATENT DOCUMENTS

| | | | |
|---|---|---|---|
| 2001/0044427 | A1 | 11/2001 | Mazel et al. |
| 2002/0004202 | A1* | 1/2002 | Cornish ............ A61K 49/0006 435/6.1 |
| 2007/0184060 | A1 | 8/2007 | Bassaganya-Riera et al. |
| 2007/0212731 | A1* | 9/2007 | Haramura ............ B01J 20/289 435/7.1 |
| 2009/0253131 | A1* | 10/2009 | Wigdal et al. ............ 435/6 |
| 2010/0132071 | A1 | 5/2010 | Hatzfeld et al. |
| 2017/0130197 | A1 | 5/2017 | Haugwitz et al. |

FOREIGN PATENT DOCUMENTS

| | | |
|---|---|---|
| WO | 1995002684 | 1/1995 |
| WO | 1996012796 | 5/1996 |
| WO | 1996013613 | 5/1996 |
| WO | 1999041258 | 8/1999 |

OTHER PUBLICATIONS

Menand et al. "Expression and disruption of the Arbidopsis TOR (target of rapamycin) gene", PNAS, vol. 99, No. 9, pp. 6422-6427, published Apr. 30, 2002.*

Wu et al., "Termination of DNA synthesis by N6-alkylated, not 3'-O-alkylated, photocleavable 2'-deoxyadenosine triphosphates", Nucleic Acids Research, vol. 35, No. 19, pp. 6339-6349, published 2007.*

Edwards et al., "Rapamycin-Binding Domain of the Protein Kinase mTOR is a Destabilizing Domain", J. Bio. Chem. May 4, 2007 vol. 282(18), pp. 13395-13401. (Year: 2007).*

Belshaw; et al. "Controlling programmed cell death with a cyclophilin-cyclosporin-based chemical inducer of dimerization", Chem Biol (Sep. 1996), 3(9):731-738.

Belshaw; et al. "Controlling protein association and subcellular localization with a synthetic ligand that induces heterodimerization of proteins", PNAS (May 1996), 93(10):4604-4607.

Blau; et al. "{gamma}-Globin gene expression in chemical inducer of dimerization (CID)-dependent multipotential cells established from human {beta}-globin locus yeast artificial chromosome ({beta}-YAC) transgenic mice", J Biol Chem (Nov. 2005), 280(44):36642-36647.

Cutler; et al. "Abscisic acid: emergence of a core signaling network", Annu Rev Plant Biol (2010), 61:651-679.

Czlapinski; et al. "Conditional glycosylation in eukaryotic cells using a biocompatible chemical inducer of dimerization", J Am Chem Soc (Oct. 2008), 130(40):13186-13187.

De Graffenried; et al. "A small-molecule switch for Golgi sulfotransferases", PNAS (Nov. 2004), 101(48):16715-16720.

Finkelstein; et al. "The *Arabidopsis* Abscisic Acid Response Gene ABI5 Encodes a Basic Leucine Zipper Transcription Factor", Plant Cell (Apr. 2000), 12(4):599-610.

Finkelstein; et al. "The *Arabidopsis* abscisic acid response locus ABI4 encodes an APETALA 2 domain protein", Plant Cell (Jun. 1998), 10(6):1043-1054.

Fujii; et al. "In vitro reconstitution of an abscisic acid signalling pathway", Nature (Dec. 2009), 462(7273):660-664.

Giraudat; et al. "Abscisic acid signaling", Curr Opin Cell Biol (Apr. 1995), 7(2):232-238, abstract only.

Harvey; et al. "Forced engagement of a RNA/protein complex by a chemical inducer of dimerization to modulate gene expression", PNAS (Feb. 2002), 99(4):1882-1887.

Hill; et al. "Abscisic Acid Structure-Activity Relationships in Barley Aleurone Layers and Protoplasts (Biological Activity of Optically Active, Oxygenated Abscisic Acid Analogs)", Plant Physiol (Jun. 1995), 108(2):573-579.

Liang; et al. "Engineering the ABA plant stress pathway for regulation of induced proximity", Sci Signal (Mar. 2011), 4(164):rs2.

Melcher; et al. "A gate-latch-lock mechanism for hormone signalling by abscisic acid receptors", Nature (Dec. 2009), 462(7273):602-608.

Miyazono; et al. "Structural basis of abscisic acid signalling", Nature (Dec. 2009), 462(7273):609-614.

Nishimura; et al. "PYR/PYL/RCAR family members are major in-vivo ABI1 protein phosphatase 2C-interacting proteins in *Arabidopsis*", Plant J (Jan. 2010), 61(2):290-299.

Nishimura; et al. "Structural mechanism of abscisic acid binding and signaling by dimeric PYR1", Science (Dec. 2009), 326(5958):1373-1379.

Oritani; et al. "A Novel Abscisic Acid Analog, (+)-(2Z, 4E)-5-(1', 4'-Dihydroxy-6', 6'-dimethyl-2'-methylenecyclohexyl)-3-methyl-2, 4-pentadienoic Acid, from Cercospora cruenta", (1984), 48(6):1677-1678.

Park; et al. "Abscisic acid inhibits type 2C protein phosphatases via the PYR/PYL family of START proteins", Science (May 2009), 324(5930):1068-1071.

Patury; et al. "Conditional nuclear import and export of yeast proteins using a chemical inducer of dimerization", Cell Biochem Biophys (2009), 53(3):127-134.

Santiago; et al. "The abscisic acid receptor PYR1 in complex with abscisic acid", Nature (Dec. 2009), 462 (7273):665-668.

Sestelo; et al. "Design and synthesis of a 1 alpha,25-dihydroxyvitamin D3 dimer as a potential chemical inducer of vitamin D receptor dimerization", Org Letter (Oct. 1999), 1(7):1005-1007.

Shibata; et al. "Crystallization of the plant hormone receptors PYL9/RCAR1, PYL5/RCAR8 and PYR1/RCAR11 in the presence of (+)-abscisic acid", Acta Crystallogr Sect F Struct Biol Cryst Commun (Apr. 2010), 66(Pt 4):456-459.

Stillwell; et al. "Abscisic acid enhances aggregation and fusion of phospholipid vesicles", Biochem Biophys Res Commun (Oct. 1988), 156(1):511-516.

Szostkiewicz; et al. "Closely related receptor complexes differ in their ABA selectivity and sensitivity", Plant J (Jan. 2010), 61(1):25-35.

Umezawa; et al. "Type 2C protein phosphatases directly regulate abscisic acid-activated protein kinases in *Arabidopsis*", PNAS (Oct. 2009), 106(41):17588-17593.

Walker-Simmons; et al. "Monoclonal antibody recognition of abscisic Acid analogs", Plant Physiol (Jan. 1991), 95(1):46-51.

Yin; et al. "Structural insights into the mechanism of abscisic acid signaling by PYL proteins", Nat Struct Mol Biol (Dec. 2009), 16(12):1230-1236.

Liang; et al., "Supplementary Materials for Engineering the ABA Plant Stress Pathway for Regulation of Induced Proximity", Science Signaling (Mar. 15, 2011), 4, rs2.

\* cited by examiner

A

B

C

MODIFIABLE CHEMICAL INDUCERS OF PROXIMITY AND METHODS OF USING THE SAME

CROSS REFERENCE TO RELATED APPLICATIONS

Pursuant to 35 U.S.C. § 119 (e), this application claims priority to the filing date of the U.S. Provisional Patent Application Ser. No. 61/700,683, filed Sep. 13, 2012; the disclosure of which is herein incorporated by reference.

INTRODUCTION

The development of small molecules that modulate protein function in a tunable fashion is of interest in chemical biology. The interactions of biomolecules such as proteins are important to the regulation of biological processes. Research tools that induce proximity of biomolecules are used for the analysis of interactions and functions of target molecules such as proteins, nucleic acids and lipid membranes. A chemical inducer of proximity (CIP) compound may be used to specifically bind two target molecules and maintain the two molecules in close proximity. Protein-protein interactions play a role in biological processes such as signal transduction pathways, apoptosis, protein activity and localization, protein secretion and inducible gene expression. For example, signaling proteins that may be activated by a CIP compound include kinases, non-kinase receptors, signaling proteases and adaptor proteins. Therefore, methods and compounds that modulate interactions of target biomolecules are of interest.

SUMMARY

Methods of reversibly inducing proximity of first and second target molecules in a sample are provided. Aspects of the methods include contacting the sample with a modifiable chemical inducer of proximity (MCIP) that reversibly induces proximity of the first and second target molecules, upon application of a stimulus that modifies the MCIP. Aspects of the invention further include methods for regulating a biological process in a cell. Aspects of the invention further include compositions, e.g., compounds and kits, etc., that find use in methods of the invention.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
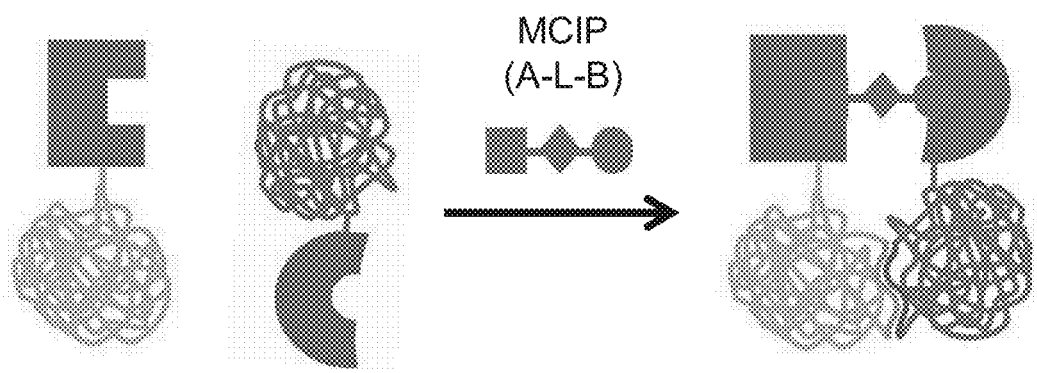
FIG. 1 depicts the reversible induction of proximity of first and second target proteins using an MCIP of formula A-L-B, where A and B are binding moieties and L is a cleavable or non-cleavable linker: (A) induction of proximity; (B) and (C) depict two embodiments of reversing induction of proximity upon application of a stimulus, e.g., by cleavage of the linker (B) or by modification of a first binding moiety that specifically binds a first target molecule (C).
Figure 1:
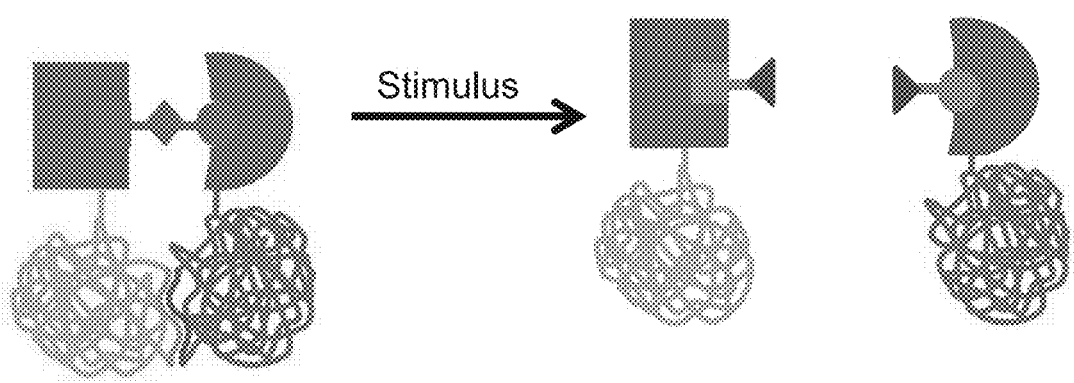
Figure 1:
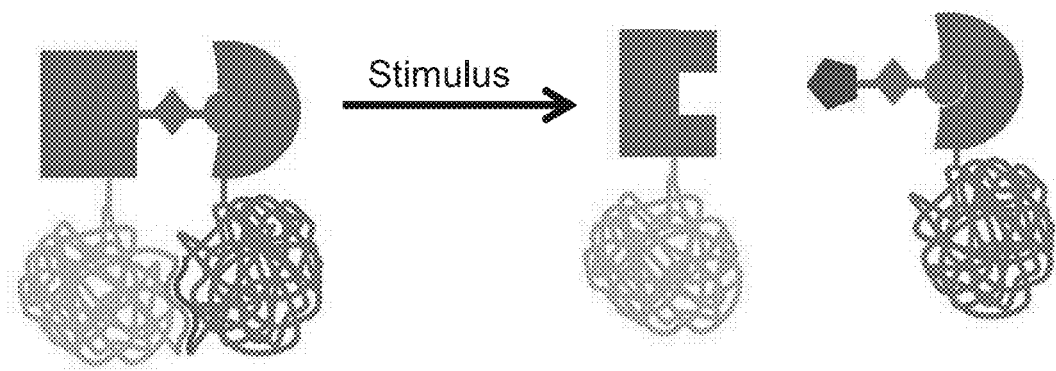
Figure 2:
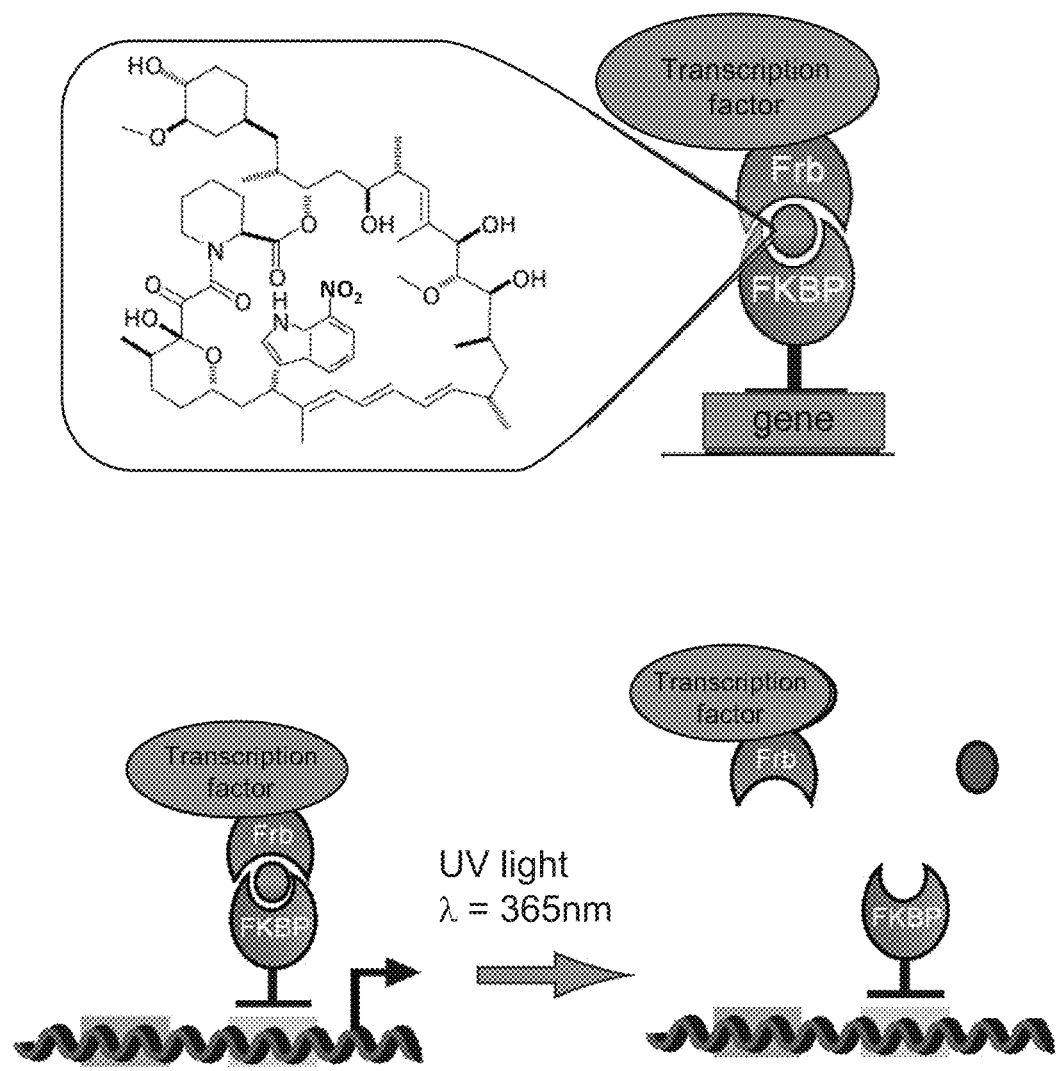
FIG. 2 illustrates the use of a rapalog-derived MCIP system to reversibly induce expression of a gene. Irradiation of the 7-nitroindolyl group of the MCIP with UV light leads to cleavage of the MCIP, dissociation of Frb and FKBP binding domains and termination of gene expression.
Figure 3:
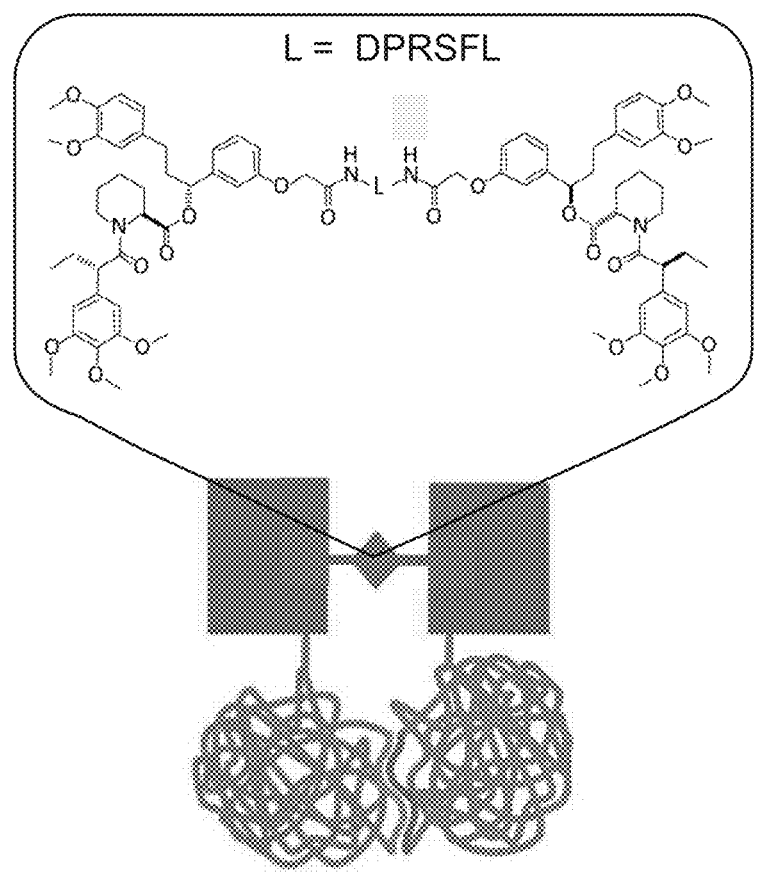
FIG. 3 illustrates the use of a homodimeric N-acyl-pipecolyl derived MCIP containing a cleavable linker L to reversibly induce proximity of first and second target proteins. The linker is cleaved upon contact with the enzyme thrombin leading to dissociation of the target proteins.
Figure 3:
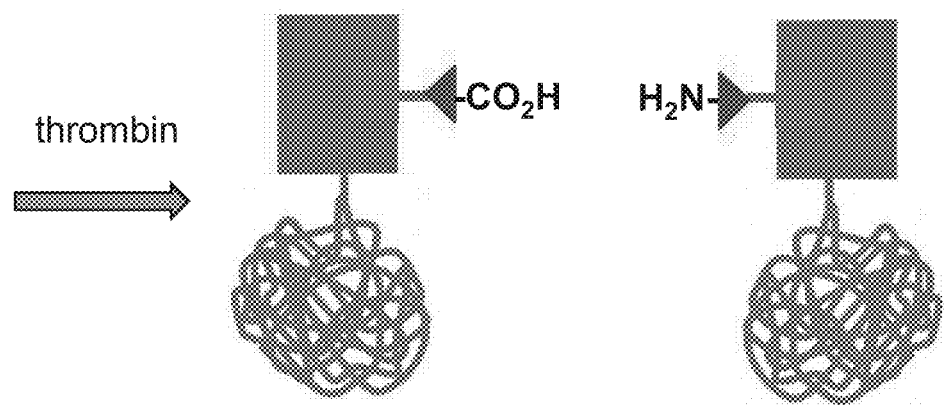
Figure 4:
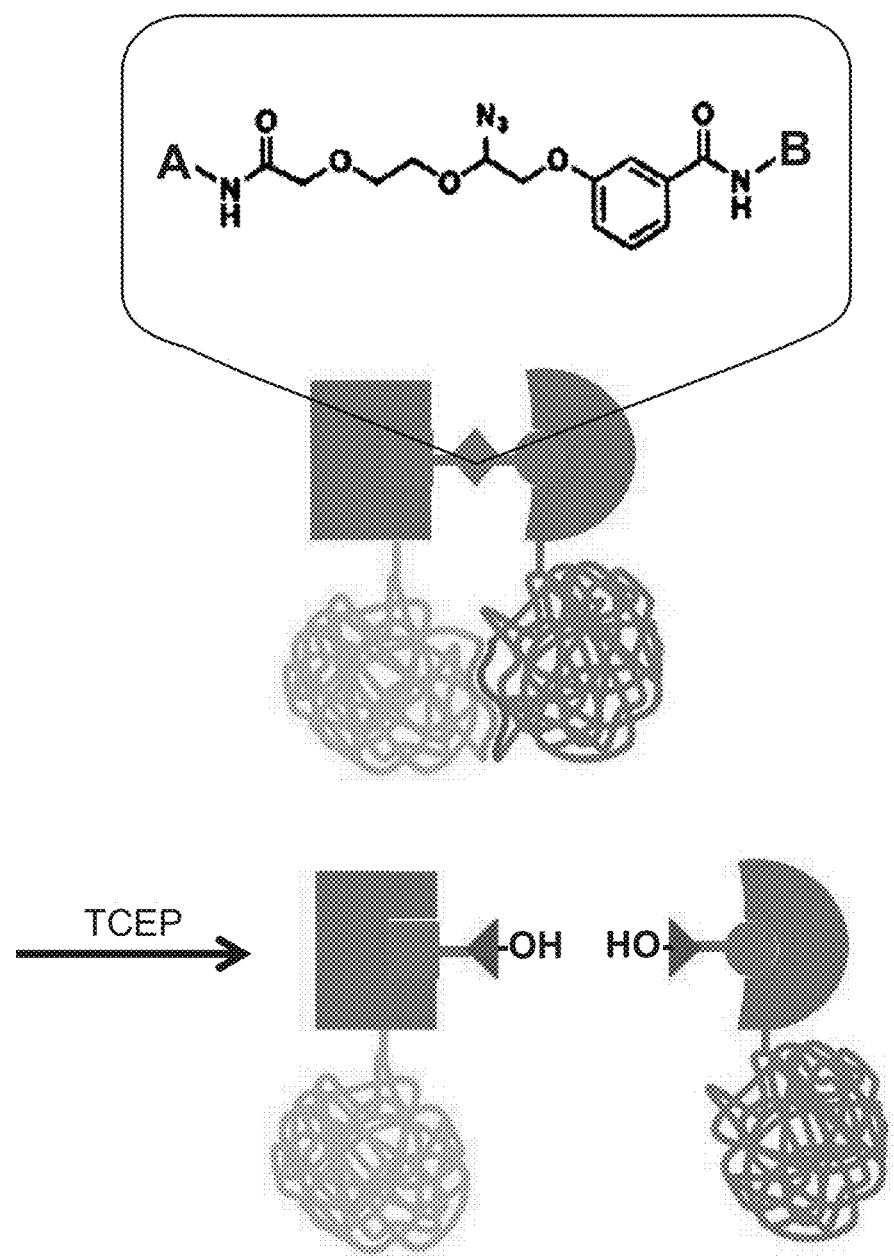
FIG. 4 illustrates the reversible induction of proximity of first and second target proteins using a MCIP of formula A-L-B where L is an azido containing linker that is cleaved upon contact with the phosphine reagent tris(2-carboxyethyl)phosphine (TCEP).

As summarized above, aspects of the invention include methods of inducing proximity of first and second target molecules in a sample. Induction of proximity of the first and second target molecules may result in the occurrence of a biological event of interest in the sample. Aspects of the invention include methods of reversibly inducing proximity using a modifiable chemical inducer of proximity (MCIP) that is modified by the application of a suitable stimulus, resulting in the spatial separation of the first and second target molecules. Embodiments of the invention include methods for regulating a biological process in a cell. Embodiments of the invention include compositions, e.g., compounds and kits, etc., that find use in the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Modifiable Chemical Inducers of Proximity (MCIPs)

As summarized above, one aspect of the invention is a modifiable chemical inducer of proximity (MCIP). A MCIP is a compound that reversibly induces proximity of at least first and second target molecules in a sample under suitable conditions, where proximity may be reversed by the application of a stimulus. Application of the stimulus to the sample modifies a modifiable group of the MCIP, thereby changing the nature of the MCIP such that the modified MCIP is no longer capable of inducing or maintaining proximity of the first and second target molecules.

By "induces proximity" is meant that two or more, such as three or more, including four or more, target molecules are spatially associated with each other through a binding event mediated by the MCIP compound. Spatial association is characterized by the presence of a binding complex that includes the MCIP and the at least first and second target molecules. In the binding complex, each member or component is bound to at least one other member of the complex. In this binding complex, binding amongst the various components may vary. In some cases, the MCIP may mediate a direct binding event between domains of first and second target molecules that would not occur in the absence of the MCIP. For example, in the presence of the MCIP, a domain of a first target molecule may bind to a domain of a second target molecule, where this binding event would not occur in the absence of the MCIP. In some instances, the MCIP binds simultaneously to the first and second target molecules, thereby producing the binding complex and desired spatial association of target molecules. In other instances, the MCIP specifically binds the first target molecule, and then the MCIP/first target molecule complex specifically binds the second target molecule. In certain cases, the MCIP may mediate an indirect binding event of the first and second target molecules, e.g., the target molecules are not in direct contact with each other but are in proximity as components of the same complex. In certain cases, the first and second target molecules are each in direct contact with the MCIP but are not in direct contact with each other.

By "reversibly induces proximity" or "reverse the induction of proximity" is meant that the spatial association of target molecules, mediated by a MCIP, may be reversed upon application of a suitable stimulus (e.g., a photon, a chemical agent or an enzyme) that modifies the MCIP. Application of a suitable stimulus results in dissociation of at least the first and second target molecule components of the binding complex. In some cases, the stimulus may be described as a modifying stimulus, e.g., a stimulus that results in modification of the modifiable group. In certain embodiments, application of a stimulus is not application of a competitive inhibitor of binding of the MCIP to a target molecule. In certain embodiments, application of a stimulus is not dilution of the sample.

In some embodiments, reversal of MCIP-mediated binding of first and second target molecules is achieved without significant dilution of the sample (e.g., without increasing the volume of the sample by 10% or more, such as 20% or more, 50% or more, 100% or more, 200% or more, 500% or more, 1000% or more (i.e., 10-fold or more)), and without addition of a competitive inhibitor of binding of the MCIP to the first and/or second target molecule.

Application of a suitable stimulus to the sample will modify the modifiable group to result in modification of the MCIP, e.g., a change in the nature of the MCIP molecule that alters its binding properties for the first and second target molecules. In some embodiments, the modified MCIP has significantly reduced affinity for the first and/or second target molecules, e.g., an affinity that is reduced by 2-fold or more, such as 3-fold or more, 4-fold or more, 5-fold or more, 10-fold or more, 30-fold or more, 50-fold or more, 100-fold or more, or even 1000-fold or more, as compared to the corresponding affinity of the unmodified MCIP. In some embodiments, the Kd value of a MCIP (e.g., a rapalog-derived or a ASC-derived MCIP), for a target molecule (e.g., a FKBP domain or a ASC binding domain) may be raised from about 10 nM or less (e.g., about 3 nM or less or about 1 nM or less) to about 20 nM or more, such as about 30 nM or more, about 40 nM or more, about 50 nM or more, about 100 nM or more, about 200 nM or more, about 500 nM or more, or even about 1 µM or more.

In some embodiments, the MCIP includes a cleavable group where application of the stimulus cleaves the cleavable group. Application of the stimulus may produce two cleaved MCIP products, where each product independently retains affinity for only one of the first and second target molecules. In some embodiments, the MCIP includes a cleavable linker connecting a first binding moiety that specifically binds the first target molecule, and a second binding moiety that specifically binds the second target molecule, such that cleavage of the linker leads to dissociation of the target molecules. In other embodiments, application of the stimulus produces a modified MCIP where one of the first and second binding moieties is changed in nature such that it has significantly reduced affinity (e.g., as described herein) for a corresponding target molecule (see e.g., FIG. 1). In such cases, the binding affinity of the other binding moiety for its target molecules may be unaffected, or alternatively, it may also be significantly reduced (e.g., as described herein).

The MCIP may include a first binding moiety (A) that specifically binds to a first target molecule and a second binding moiety (B) that specifically binds to a second target molecule, and a modifiable group (X). A MCIP of the invention may be described by formula (I):

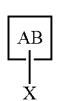 (I)

wherein A is a first binding moiety, B is a second binding moiety and X is a modifiable group. In certain embodiments, in formula (I), X may be a part of A or a part of B, or X may be connected to A and/or B via a linker. In some instances, the MCIP specifically binds the first and second target molecules independently, e.g., formation of a ternary complex may occur via initial binding of the MCIP to either the first or the second target molecule. In other instances, specific binding of the MCIP to the second target molecule is dependent on prior formation of a MCIP/first target molecule complex. In this context, by "dependent" is meant that the second target molecule has a higher affinity for the complex of MCIP/first target molecule than it has for the MCIP alone. In some embodiments, MCIPs which form such ternary complexes include a first binding moiety (A) that specifically binds a first protein domain (e.g., a rapalog that specifically binds a FKBP domain, or an alkenyl substituted cycloaliphatic (ASC) inducer compound that specifically binds an PYL ASC binding domain), and the second binding moiety (B) that specifically binds a second protein domain (e.g., a rapalog that specifically binds a FRB domain, or an ASC inducer compound that specifically binds an ABI ASC binding domain) where binding of the second protein domain is dependent on the prior binding of A and the first protein domain. In certain cases, the complex of MCIP/first target protein specifically binds the second target protein without direct contacts being formed between the MCIP and the second target protein. In such cases, the MCIP mediates the binding of first and second target proteins.

The modifiable group (X) may be included at any convenient position in the structure of an MCIP. In some cases, the modifiable group (X) is part of the first binding moiety (A) or is part of the second binding moiety (B). In some cases, X may be included in that part of the structure which specifically binds the first target molecule (e.g., a FKBP domain or ASC binding domain), or alternatively, may be included in that part of the structure which specifically binds the second target molecule (e.g., a FRB domain or a ASC binding domain). In other cases, X may be separate from the binding moieties A and B. As such, X may be located at a position of the structure that is not involved in specific binding interactions with the first or second target molecules, e.g., in a linker that connects A and B.

In some embodiments, the MCIP is described by one of the following formulas:

X-A-B (II)

A-B-X (III)

A-X-B (IV)

wherein A is a first binding moiety, B is a second binding moiety and X is a modifiable group (X). In formulas (II), (III) and (IV), X, A and B may be connected via linkers. In some cases, A and B are homologous. In other cases, A and B are heterologous.

In some cases, the first and second binding moieties (A and B) may be connected via a linker that includes a modifiable group. In other cases, the linker does not include a modifiable group. In certain embodiments, the MCIP is described by formula:

A-L-B (V)

wherein A is a first binding moiety, B is a second binding moiety and L is a linker that includes a modifiable group (X). As such, in certain cases where the modifiable group is cleavable, the linker (L) is a cleavable linker, e.g., a photocleavable or enzymatically cleavable linker. In formula (V), the MCIP may be homodimeric, where the first and second binding moieties are homologous, or heterodimeric where the first and second binding moieties are heterologous.

Binding Moieties

The subject MCIPs may include a first binding moiety (A) that specifically binds to a first target molecule, a second binding moiety (B) that specifically binds to a second target molecule, and a modifiable group (X). Any convenient binding moieties that specifically bind a target molecule of interest may be adapted for use in MCIPs of the invention. A variety of binding moieties are available for use in the subject MCIPs, including ligands of target biomolecules, such as ligands that specifically bind to particular DNA, RNA, carbohydrates, lipids, or proteins of interest (such as, e.g., protein domains of interest), transcription factor DNA binding domains, other protein: protein interaction domains, such as SH2 domains, Paz domains, RING domains, the domains listed at the website produced by placing "http://" before "pawsonlab.mshri.on.ca/ index.php?option=com_content&task=view&id=30& Itemid=63/", etc. In some cases, binding moieties include, but are not limited to: small molecules (such as, e.g., a chemotherapeutic drug, a lipid, a sugar, an amino acid, or a nucleotide), peptides, oligonucleotides, ligands, receptor agonists, receptor antagonists, biotin, rapamycin, FK506, cyclosporine A, rapalogs, alkenyl substituted cycloaliphatic (ASC) inducer compounds, N-oxalyl-pipecolyl and N-oxalyl-prolyl compounds.

The terms "specific binding," "specifically binds," and the like, refer to the ability of one binding moiety to preferentially bind directly to the other binding moiety relative to other molecules or moieties in the cell. In certain embodiments, the affinity between a given binding moiety and the molecule or moiety to which it specifically binds when they are specifically bound to each other in a binding complex is characterized by a $K_D$ (dissociation constant) of $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, or $10^{-15}$ M or less (it is noted that these values can apply to any specific binding pair interactions mentioned elsewhere in this description, in certain embodiments).

A wide variety of compounds, including both naturally occurring and synthetic substances, can be adapted for use as MCIPs. Applicable and readily observable or measurable criteria for selecting a compound for use as a MCIP may include: (A) the compound is physiologically acceptable (e.g., lacks undue toxicity towards the cell or animal for which it is to be used); (B) it has a reasonable therapeutic dosage range; (C) it can cross the cellular and other membranes, as necessary, and (D) binds to the target domains of the target molecules for which it is designed with reasonable affinity for the desired application. A first desirable criterion is that the compound is relatively physiologically inert, but for its MCIP activity. In some instances, the MCIP will be non-peptide and non-nucleic acid. Of interest in some applications are compounds that can be taken orally (e.g., compounds that are stable in the gastrointestinal system and can be absorbed into the vascular system).

MCIP compounds of interest include small molecules. By small molecule is meant a molecule having a molecular weight of 5000 daltons or less, such as 2500 daltons or less, including 1000 daltons or less, e.g., 500 daltons or less. In certain instances, the compounds are non-toxic, e.g., when administered to a living subject. For example, in certain of such embodiments, the MCIPs exhibit substantially no, if any, toxicity at concentrations of 1 g or more/kg body weight, such as 2.5 g or more/kg body weight, including 5 g or more/kg body weight.

By "adapted for use" is meant that a binding moiety or compound of interest may be modified using any convenient method to include one or more modifiable group(s) as described herein. The binding moiety or compound of interest may be modified by replacing a suitable existing group with a modifiable group, e.g., a photoactive nitro-indolyl group may be utilized to replace an existing indolyl substituent of the compound. In some cases, the modifications may be selected such that the modifiable group that is introduced is of a similar size and/or structure as the substituent of the compound from which it derives. In other cases, the modifiable group is introduced at positions of the binding moiety or compound that are tolerant to groups of different sizes and/or structures. The modifiable groups may be introduced at any convenient position of the binding moieties or compounds. In some cases, the modifiable group and the position at which it is introduced in the binding moiety or compound are selected such that the MCIP produced specifically binds a target molecule of interest. In certain embodiments, the target molecule includes a protein domain where specific binding to the MCIP is optimized by modification of the protein domain, e.g., by mutation of the binding residues.

In some embodiments, the MCIP is derived from a suitable chemical inducer of proximity (CIP), e.g., a rapalog or an alkenyl substituted cycloaliphatic (ASC) based CIP. Any convenient compound that functions as a chemical inducer of proximity (CIP) may be adapted to include a modifiable group and employed in the subject methods.

Rapalog-Derived MCIPs

One type of CIP of interest is a compound (as well as homo- and hetero-oligomers (e.g., dimers) thereof), that is capable of binding to an FKBP protein and/or to a cyclophilin protein. Such compounds include, but are not limited to: cyclosporin A, FK506, FK520, and rapamycin, and derivatives thereof. Many derivatives of such compounds are already known, including synthetic analogs of rapamycin, which can be adapted for use in the subject methods as desired.

In some embodiments, the MCIP is a rapamycin analog (i.e., a rapalog). Any suitable rapalog may be modified for use as a MCIP in the subject methods. As used herein, the term "rapalogs" refers to a class of compounds comprising the various analogs, homologs and derivatives of rapamycin and other compounds related structurally to rapamycin. Rapalogs include but are not limited to, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and preferably do not contain an oxygen bridge between C1 and C30.

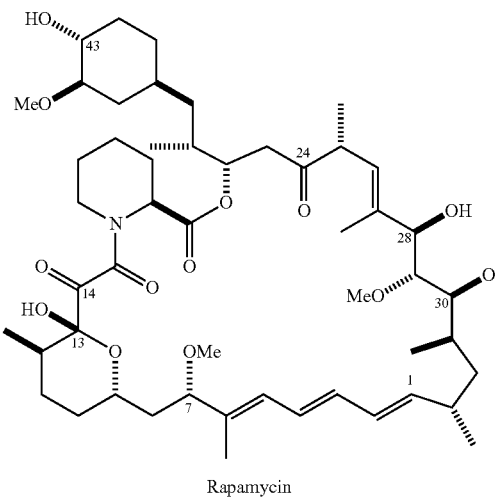

Rapamycin

Rapalogs that may be adapted to find use as MCIPs in embodiments of the invention include, but are not limited to, those compounds described in: U.S. Pat. Nos. 7,067,526; and 7,196,192; the disclosures of which are herein incorporated by reference.

Further illustrative examples of rapalogs are disclosed in the following documents: U.S. Pat. Nos. 6,693,189; 6,984,635; WO9641865, WO9710502, WO9418207, WO9304680, U.S. Pat. Nos. 5,527,907, 5,225,403, WO9641807, WO9410843, WO9214737, U.S. Pat. Nos. 5,484,799, 5,221,625, WO9635423, WO9409010, WO9205179, U.S. Pat. Nos. 5,457,194, 5,210,030, WO9603430, WO9404540, U.S. Pat. Nos. 5,604,234, 5,457, 182, 5,208,241, WO9600282, WO9402485, U.S. Pat. Nos. 5,597,715, 5,362,735, 5,200,411, WO9516691, WO9402137, U.S. Pat. Nos. 5,583,139, 5,324,644, 5,198, 421, WO9515328, WO9402136, U.S. Pat. Nos. 5,563,172, 5,318,895, 5,147,877, WO9507468, WO9325533, U.S. Pat. Nos. 5,561,228, 5,310,903, 5,140,018, WO9504738, WO9318043, U.S. Pat. Nos. 5,561,137, 5,310,901, 5,116, 756, WO9504060, WO9313663, U.S. Pat. Nos. 5,541,193, 5,258,389, 5,109,112, WO9425022, WO9311130, U.S. Pat. Nos. 5,541,189, 5,252,732, 5,093,338, WO9421644, WO9310122, U.S. Pat. Nos. 5,534,632, 5,247,076, and 5,091,389, the disclosures of which are herein incorporated by reference.

In some embodiments, a rapalog of interest is adapted to include a modifiable group (e.g., a photoreactive group such as a photocleavable group). The modifiable group may be located at any suitable position of the rapalog structure, e.g., the C7 or C3 position. C7 and C3 rapalogs that may be adapted for use in the subject methods include those described by Crabtree et al., "Rapamycin analogs with differential binding specificity permit orthogonal control of protein activity," Chemistry & Biology 13, 99-107, 2006, and U.S. Pat. No. 6,984,635, the disclosures of which are herein incorporated by reference. Note that Crabtree et al., sometimes use an alternative C16/C20 numbering system.

In some embodiments, a C3-rapalog of interest is of the structure:

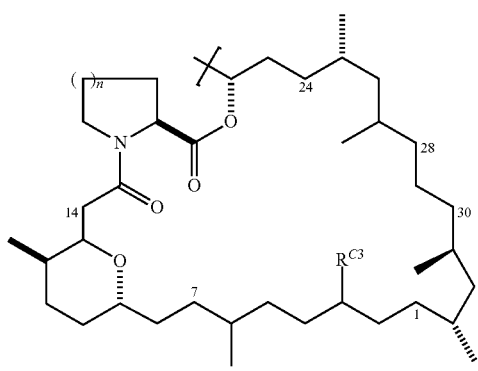

n = 1 or 2 bearing one or more optional substituents, and typically unsaturated at one or more carbon—carbon bonds spanning carbons 1 through 8, as a substantially pure stereoisomer or mixture of stereoisomers, where $R^{C3}$ is other than H, as those terms are defined in U.S. Pat. No. 6,984,635. For example, in various embodiments of the invention, $R^{C3}$ is a substituted or unsubstituted aliphatic, heteroaliphatic, aromatic or heteroaromatic moiety, as those terms are defined in U.S. Pat. No. 6,984,635.

In some embodiments, a C7-rapalog of interest is of one of the following structures:

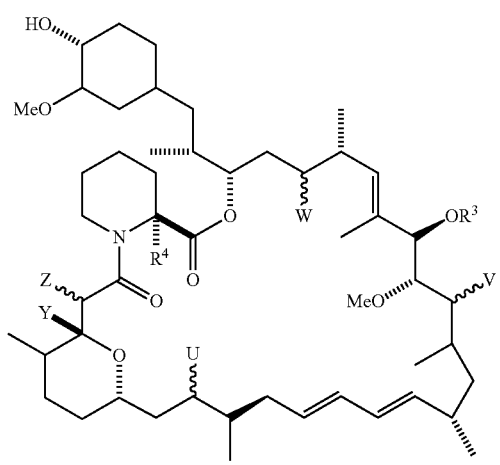

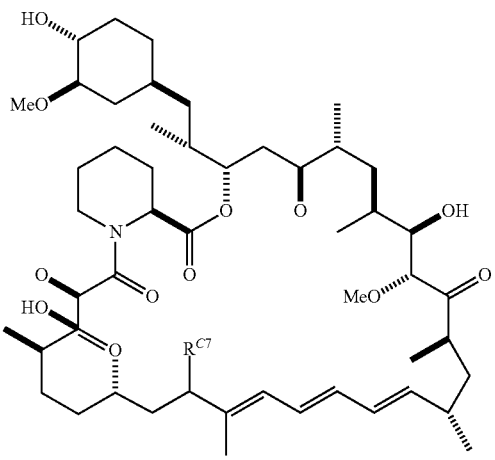

wherein $R^{C7}$ is a substituted or unsubstituted aliphatic, heteroaliphatic, aromatic or heteroaromatic moiety; and wherein U is —H, —$OR^1$, —$SR^1$, —$OC(O)R^1$, —OC(O)$NHR^1$, —$NHR^1$, —$NHC(O)R^1$, $NHSO2$-$R^1$ or —$R^2$; $R^2$ is a substituted aryl or allyl or alkylaryl (e.g. benzyl or substituted benzyl); V is —$OR^3$ or (=O); W is =O, =$NR^4$, =$NOR^4$, =$NNHR^4$, —$NHOR^4$, —$NHNHR^4$, —$OR^4$, —$OC(O)R^4$, —$OC(O)NR^4$ or —H; Y is —$OR^5$, —$OC(O)R^5$ or —$OC(O)NHR^5$; Z is =O, —$OR^6$, —$NR^6$, —H, —NC(O)$R^6$, —$OC(O)R^6$ or —$OC(O)NR^6$; $R^3$ is H, —$R^7$, —$C(O)R^7$, —$C(O)NHR^7$ or C-28/C-30 cyclic carbonate; and $R^4$ is H or alkyl; where $R^1$, $R^4$, $R^5$, $R^6$ and $R^7$ are independently selected from H, alkyl, alkylaryl or aryl; as those terms are defined in WO 96/41865. A number of rapalogs are specifically disclosed in that document.

In some embodiments, the subject MCIP is adapted from a rapalog as described in U.S. Pat. No. 7,067,526. In certain embodiments, the subject MCIP is of one of the following structures:

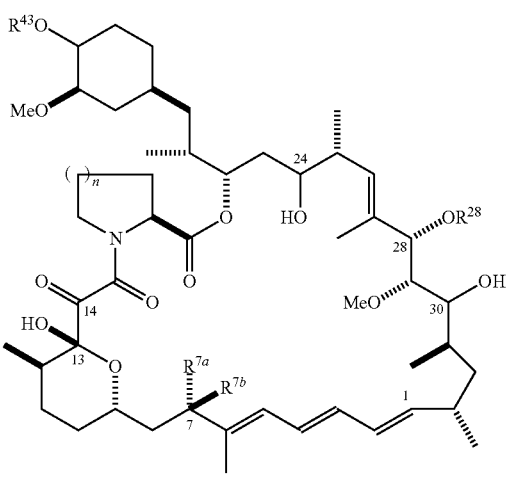

-continued

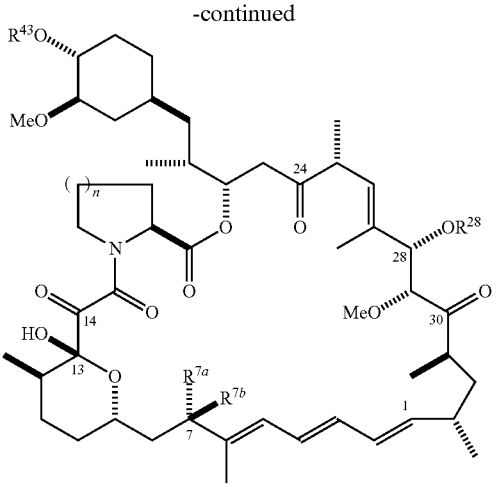

wherein n is 1 or 2; $R^{28}$ and $R^{43}$ are independently selected from the group consisting of H and an aliphatic or acyl moiety; one of $R^{7a}$ and $R^{7b}$ is H and the other is halo, —$R^A$, —$OR^A$, —$SR^A$, —$OC(O)R^A$, —$OC(O)NR^AR^B$— $NR^AR^B$, —NR $C(O)R^A$, —$NR^BC(O)OR^A$, —$NR^BSO_2R^A$, —$NR^BSO2NR^AR^{B'}$ or —$NRBC(O)NR^AR^{B'}$; or $R^{7a}$ and $R^{7b}$ taken together, are H in the tetraene moiety:

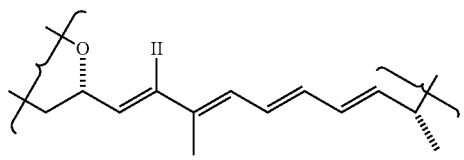

where $R^A$ is H or an aliphatic, heteroaliphatic, aryl, or heteroaryl moiety; where $R^B$ is H, OH or an aliphatic, heteroaliphatic, aryl, or heteroaryl moiety; where each aliphatic moiety is an independently chosen saturated or unsaturated, branched or unbranched, cyclic or polycyclic, aliphatic hydrocarbon containing 1-8 contiguous aliphatic carbon atoms; where each heteroaliphatic moiety is an independently chosen 2-8-membered non-cyclic or 3-10-membered cyclic aliphatic moiety which contains one or more oxygen, sulfur, nitrogen, phosphorous or silicon atoms; where each aryl moiety is an independently chosen 6-14-membered mono- or polycyclic unsaturated moiety; where each heteroaryl moiety is an independently chosen 5-6-membered monocyclic or 9-14-membered polycyclic unsaturated moiety which contains one or more oxygen, sulfur or nitrogen atoms; and where each acyl moiety is an independently chosen —OCR group where R is an aliphatic, heteroaliphatic, aryl, or heteroaryl moiety; wherein each alkyl, alkenyl or acyl moiety contains one or more optional substituents selected from the group consisting of —OH, —$OR^2$, —SH, —$SR^2$, —CHO, =O, —COOH (or ester, carbamate, urea, oxime or carbonate thereof), —$NH_2$ (or substituted amine, amide, urea, carbamate or guanidino derivative thereof), halo, trihaloalkyl, cyano, —$SO_2$—CF3, —$OSO_2F$, —$OS(O)_2R^{11}$, —$SO_2$—$NHR^{11}$, $NHSO_2R^{11}$, sulfate, sulfonate, aryl and heteroaryl moieties; where $R^2$ is an aliphatic, heteroaliphatic, aryl, heteroaryl or alkylaryl moiety; and where $R^{11}$ is H or an aliphatic, heteroaliphatic, aryl or heteroaryl moiety; or a pharmaceutically acceptable salt thereof;

wherein each group and substituent is as defined in U.S. Pat. No. 7,067,526, and wherein the compound is adapted for use to include a modifiable group, e.g., as described herein. In certain embodiments, the rapalogs of U.S. Pat. No. 7,067,526, e.g., as described above, are adapted to include a modifiable group at the $R^{7a}$ or $R^{7b}$ positions.

In some embodiments, the MCIP is a cleavable rapamycin analog (i.e., a rapalog that has been adapted to include a cleavable group). In certain embodiments, a rapalog is adapted to include a nitro-aryl group at the C7 position, such as a nitro-indole group, e.g., a 3-nitro-indole, a 4-nitro indole, a 5-nitro indole, a 6-nitro-indole or a 7-nitro-indole group, where the indole ring may be further substituted, e.g., with a methyl group, e.g., at the 3- or 7-position. In certain embodiments, the following structure describes a rapalog-derived MCIP of the invention that includes a 7-nitro-indole group at the C7 position:

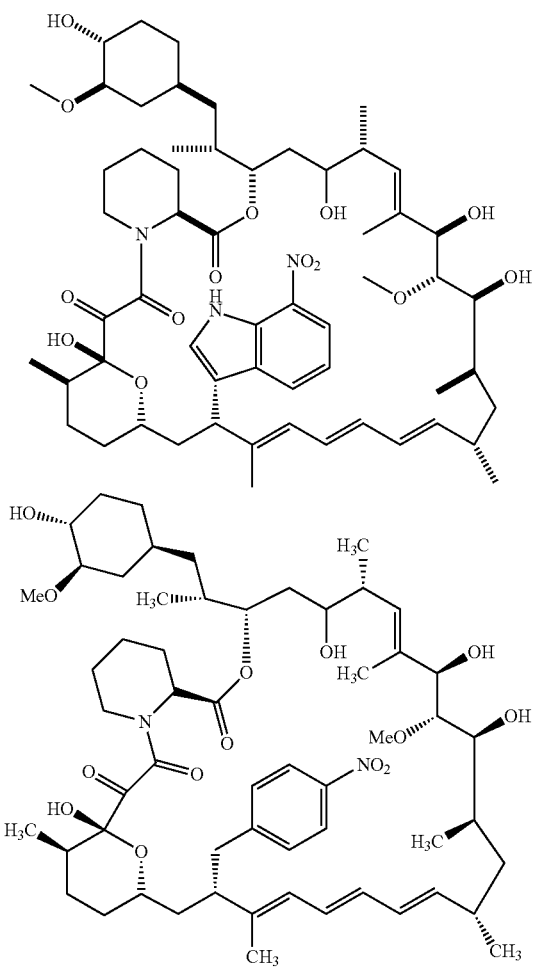

Alkenyl Substituted Cycloaliphatic Derived MCIPs

Another type of CIP compound of interest is an alkenyl substituted cycloaliphatic (ASC) inducer compound. ASC inducer compounds include a cycloaliphatic ring substituted with an alkenyl group. In certain embodiments, the cycloaliphatic ring is further substituted with a hydroxyl and/or oxo group. In some cases, the carbon of the cycloaliphatic ring that is substituted with the alkenyl group is further substituted with a hydroxyl group. The cycloaliphatic ring system may be an analog of a cyclohex-2-enone ring system.

In some embodiments, the ASC inducer compound includes a cyclohexene or a cyclohexane ring, such as is found in a cyclohexenone group (e.g. a cyclohex-2-enone), a cyclohexanone group, a hydroxy-cyclohexane group, a hydroxy-cyclohexene group (e.g., a cyclohex-2-enol group) or a methylenecyclohexane group (e.g. a 3-methylenecyclohexan-1-ol group); where the cycloaliphatic ring is substituted with an alkenyl group of about 2 to 20 carbons in length, that includes 1, 2, 3, 4, 5, 6, 7, 8, 9 or 10 unsaturated bonds. In certain embodiments, the alkenyl substituent includes a conjugated series of unsaturated bonds. In particular embodiments, the alkenyl substituent may be 4 carbons in length and include 2 conjugated double bonds. In another embodiment, the alkenyl substituent is conjugated to the cycloaliphatic ring system. Further details of such compounds are disclosed in WO/2011/163029; the disclosure of which is herein incorporated by reference.

In certain embodiments, the MCIP is derived from an ASC described by formula (VII):

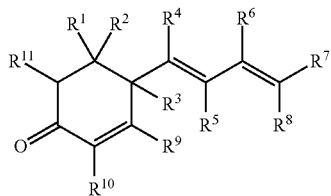

(VII)

wherein $R^1$, $R^2$, $R^3$, $R^4$, $R^5$, $R^6$, $R^7$, $R^8$, $R^9$, $R^{10}$ and $R^{11}$ are independently selected from hydrogen, an alkyl, an aryl, an alkenyl, an alkynyl, a carbonyl, an acyl, a halogen, a hydroxy, an alkoxy, an aryloxy, and a heterocyclic group and any two of $R^1$, $R^2$, $R^3$, $R^4$, $R^5$, $R^6$, $R^7$, $R^8$, $R^9$, $R^{10}$ and $R^{11}$ can optionally be cyclically linked; as those terms are defined in WO/2011/163029; and wherein the compound is adapted for use to include a modifiable group, e.g., as described herein. In certain instances, the MCIP is derived from abscisic acid.

In some embodiments, the MCIP is derived from an ASC of the structure of formula (VIII):

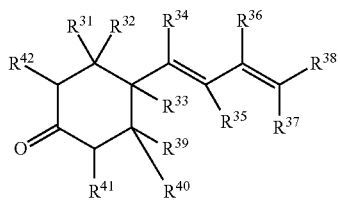

(VIII)

where $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ are independently selected from hydrogen, an alkyl, an aryl, an alkenyl, an alkynyl, a carbonyl, an acyl, a halogen, a hydroxy, an alkoxy, an aryloxy, a heterocyclic group, where optionally any two of $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ can be cyclically linked; where the compound is adapted for use to include a modifiable group, e.g., as described herein.

In some embodiments, in formula (VIII), $R^{31}$, $R^{32}$, $R^{34}$, $R^{35}$, $R^{36}$, $R^{37}$, $R^{39}$, $R^{40}$, $R^{41}$ and $R^{42}$ are independently selected from hydrogen, an alkyl and a halogen (e.g., fluoro). In some embodiments, in formula (VIII), $R^{38}$ is selected from hydrogen, carboxy, an ester, a hydroxymethyl, formyl and an alkenyl (e.g., —CH=CHCOCH$_3$). In some embodiments, in formula (VIII), $R^{33}$ is selected from hydrogen, hydroxy, and an alkoxy. In some embodiments, in formula (VIII), $R^{36}$ and $R^{37}$ are cyclically linked (e.g., to form a cyclopentene ring).

In some embodiments, the MCIP is derived from an ASC of the structure of formula (IX):

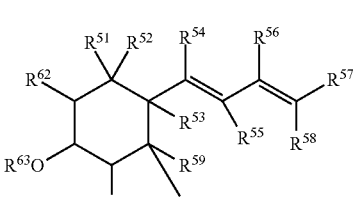

(IX)

where $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$ and $R^{63}$ are independently selected from hydrogen, an alkyl, an aryl, an alkenyl, an alkynyl, a carbonyl, an acyl, a halogen, a hydroxy, an alkoxy, an aryloxy, a heterocyclic group, where optionally any two of $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$ and $R^{63}$ can be cyclically linked; where the compound is adapted for use to include a modifiable group, e.g., as described herein.

In some embodiments, in formula (IX), $R^{51}$, $R^{52}$, $R^{54}$, $R^{55}$, $R^{56}$, $R^{58}$, $R^{59}$, $R^{60}$, $R^{61}$ and $R^{62}$ are independently selected from hydrogen, an alkyl and a halogen (e.g., fluoro). In some embodiments, in formula (IX), $R^{57}$ is selected from hydrogen, carboxy, an ester, a hydroxymethyl, formyl and an alkenyl (e.g., —CH=CHCOCH$_3$). In some embodiments, in formula (IX), $R^{53}$ is selected from hydrogen, hydroxy, and an alkoxy. In some embodiments, in formula (IX), $R^{63}$ is selected from hydrogen, an alkyl, and an acyl. In some embodiments, in formula (IX), $R^{56}$ and $R^{58}$ are cyclically linked (e.g., to form a cyclopentene ring). In some embodiments, in formula (IX), $R^{53}$ and $R^{59}$ are cyclically linked (e.g., to form an epoxide). In some embodiments, in formula (IX), $R^{52}$ and $R^{59}$ are cyclically linked (e.g., to form an ether bridge).

In certain embodiments, the MCIP is derived from an ASC of the structure of formula (X):

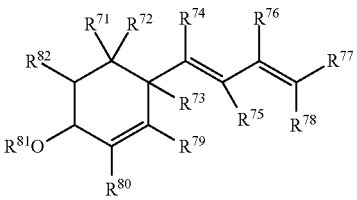

(X)

where $R^{71}$, $R^{72}$, $R^{73}$, $R^{74}$, $R^{75}$, $R^{76}$, $R^{77}$, $R^{78}$, $R^{79}$, $R^{80}$, $R^{81}$ and $R^{82}$ are independently selected from hydrogen, an alkyl, an aryl, an alkenyl, an alkynyl, a carbonyl, an acyl, a halogen, a hydroxy, an alkoxy, an aryloxy, a heterocyclic group, where optionally any two of $R^{71}$, $R^{72}$, $R^{73}$, $R^{74}$, $R^{75}$, $R^{76}$, $R^{77}$, $R^{78}$, $R^{79}$, $R^{80}$, $R^{81}$ and $R^{82}$ can be cyclically linked; where the compound is adapted for use to include a modifiable group, e.g., as described herein.

In particular embodiments, in formula (X), $R^{71}$, $R^{72}$, $R^{74}$, $R^{75}$, $R^{76}$, $R^{78}$, $R^{79}$, $R^{80}$ and $R^{82}$ are independently selected from hydrogen, an alkyl and a halogen (e.g., fluoro). In particular embodiments, in formula (X), $R^{77}$ is selected from hydrogen, carboxy, an ester, a hydroxymethyl, formyl and an alkenyl (e.g., —CH=CHCOCH$_3$). In particular embodiments, in formula (X), R$^{73}$ is selected from hydrogen, hydroxy, and an alkoxy. In particular embodiments, in formula (X), R$^{81}$ is selected from hydrogen, an alkyl, and an acyl. In particular embodiments, in formula (X), R$^{76}$ and R$^{78}$ are cyclically linked (e.g., to form a cyclopentene ring).

In certain embodiments, the MCIP is derived from an ASC of the structure of formula (XI):

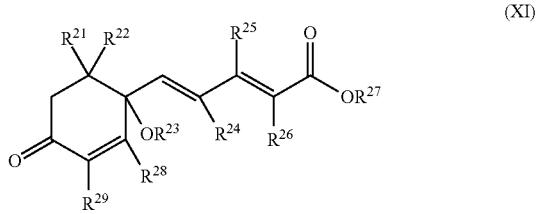

where R$^{21}$, R$^{22}$, R$^{23}$, R$^{24}$, R$^{25}$, R$^{26}$, R$^{27}$, R$^{28}$ and R$^{29}$ are independently selected from hydrogen, a halogen (e.g., fluoro), an alkyl (e.g., a lower alkyl or a hydroxymethylene), an alkoxy, a hydroxy, an alkynyl, an alkenyl, a hydroxymethyl, a trifluoromethyl; where optionally any two of adjacent where R$^{21}$, R$^{22}$, R$^{23}$, R$^{24}$, R$^{25}$, R$^{26}$, R$^{27}$, R$^{28}$ and R$^{29}$ can be cyclically linked; where the compound is adapted for use to include a modifiable group, e.g., as described herein.

In particular embodiments, in formula (XI), R$^{21}$, R$^{22}$, R$^{24}$, R$^{25}$, R$^{26}$, R$^{28}$ and R$^{29}$ are independently selected from hydrogen, an alkyl and a halogen (e.g., fluoro); and R$^{23}$ and R$^{27}$ are independently selected from hydrogen and an alkyl. In particular embodiments, in formula (XI), R$^{21}$ and R$^{22}$ are independently selected from hydrogen, a lower alkyl (e.g., a methyl, a hydroxymethyl, a trifluoromethyl, a difluoromethyl), a halogen (e.g., a fluoro), hydroxy, an alkoxy, an alkenyl, and an alkynyl (e.g., an acetylenyl, —CCH). In particular embodiments, in formula (XI), R$^{23}$ is selected from hydrogen and a lower alkyl (e.g., a methyl). In particular embodiments, in formula (XI), R$^{24}$ is hydrogen. In particular embodiments, in formula (XI), R$^{25}$ is selected from hydrogen, a lower alkyl (e.g., a methyl or a hydroxymethyl) and a halogen (e.g., a fluoro). In particular embodiments, in formula (XI), R$^{26}$ is selected from hydrogen and a halogen (e.g., fluoro). In particular embodiments, in formula (XI), R$^{27}$ is selected from hydrogen and a lower alkyl (e.g., a methyl or an ethyl). In particular embodiments, in formula (XI), R$^{28}$ is selected from hydrogen, a lower alkyl (e.g., a methyl, an ethyl or a hydroxymethyl). In particular embodiments, in formula (XI), R$^{29}$ is selected from hydrogen and a halogen (e.g., fluoro, chloro, bromo or iodo). In particular embodiments, in formula (XI), R$^{27}$ is selected from hydrogen In certain embodiments the MCIP is derived from an ASC of the following structure:

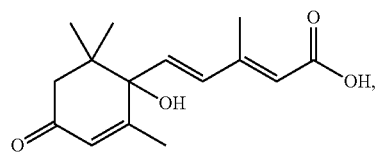 [SMILES: CC1=CC(=O)CC(C)(C)C1(O)/C=C/C(C)=C/C(=O)O]

or a substituted derivative thereof; where the compound is adapted for use to include a modifiable group, e.g., as described herein.

In particular embodiments, the MCIP is derived from an ASC of the following structure:

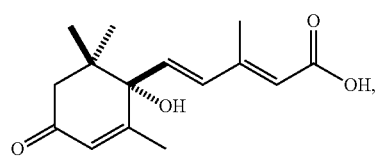

or a substituted derivative thereof; where the compound is adapted for use to include a modifiable group, e.g., as described herein.

Specific ASC inducer compounds that may be adapted for use in the subject methods include, but are not limited to: abscisic acid, abscisic aldehyde, abscisic alcohol, methyl abscisate, ethyl abscisate, xanthoxin, phaseic acid, dihydrophaseic acid, epi-dihydrophaseic acid, methyl phaseate, ethyl phaseate, alpha-ionone, beta-ionone, damascene, beta-damascenone, 4'-oxo-alpha-ionylideneacetic acid, 4'-hydroxy-alpha-ionylideneacetic acid, alpha-ionylideneacetic acid, epoxy-beta-ionylideneacetic acid, 2',3'-dihydroabscisic acid, 7'-hydroxyabscisic acid, 8'-hydroxyabscisic acid, 8'-hydroxy-2',3'-dihydroabscisic acid, and substituted derivatives thereof, as defined in WO/2011/163029.

FK506 and Cyclosporin a Derived MCIPs

Another type of CIP compound of interest is a FK506-type ligand or a cyclosporin A-type ligand containing compound. FK506-type ligand and cyclosporin A-type ligand containing compounds include those compounds described by Crabtree et al. in WO 1994/018317, the disclosure of which is herein incorporated by reference. In some embodiments, the MCIP is derived from a FK506-type ligand or a cyclosporine A-type ligand as described in one of FIGS. 9A-D, 10A-B, 11A-F, 13A-B, 16A-D, 17 and 23 of WO 1994/018317.

In certain embodiments, the MCIP is derived from a FK506-type dimer described by the following structure 5:

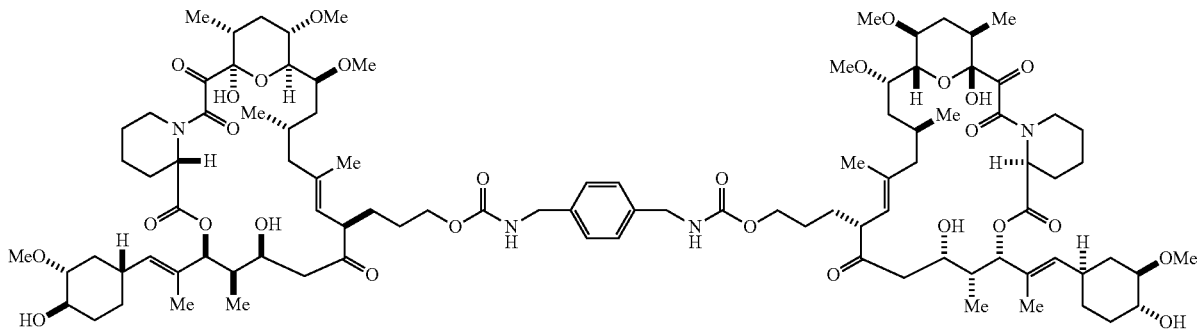

N-Oxalyl-Pipecolyl and N-Oxalyl-Prolyl Derived MCIPs

Another type of CIP compound of interest is an N-oxalyl-pipecolyl or N-oxalyl-prolyl-type compound. N-oxalyl-pipecolyl and N-oxalyl-prolyl-type compounds include immunophilin multimerizing agents described in WO 1996/06097, the disclosure of which is herein incorporated by reference. In some embodiments, the MCIP is derived from an immunophilin multimerizing agents of the following formula:

$$M^1\text{-}L^2\text{-}M^2$$

where $M^1$ and $M^2$ are independently moieties of the following formula:

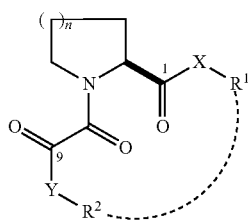

where n is 1 or 2;
X is O, NH or CH$_2$;
Y is O, NH, NR$^3$, or represents a direct, i.e., covalent, bond from R$^2$ to atom 9;
R$^1$, R$^2$ and R$^3$ are independently C$_1$-C$_{20}$ alkyl or aryl;
where alkyl is intended to include both saturated and unsaturated straight chain, branched, cyclic, or polycyclic aliphatic hydrocarbons which may contain oxygen, sulfur, or nitrogen in place of one or more carbon atoms, and which are optionally substituted with one or more functional groups selected from the group consisting of hydroxy, C$_1$-C$_8$ alkoxy, acyloxy, carbamoyl, amino, N-acylamino, ketone, halogen, cyano, carboxyl, and aryl (unless otherwise specified, the alkyl, alkoxy and acyl groups preferably contain 1-6 contiguous aliphatic carbon atoms);

aryl is intended to include stable cyclic, heterocyclic, polycyclic, and polyheterocyclic unsaturated C$_3$-C$_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, C$_1$-C$_8$ alkoxy, C$_1$-C$_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry); R$^1$ and R$^2$ may optionally be joined, i.e., covalently linked, together, forming a macrocyclic structure (as indicated by the dashed line in the formula); and L$^2$ is a linker moiety covalently linking monomers M$^1$ and M$^2$ through covalent bonds to either R$^1$ or R$^2$, not necessarily the same in each of M$^1$ and M$^2$; wherein each group and substituent is as defined in WO 1996/06097; where the compound is adapted for use to include a modifiable group, e.g., as described herein. Any one of M$^1$, M$^2$ or L$^2$ is adapted to include a modifiable group, as described herein. In some cases, L$^2$ is adapted to include a cleavable group (e.g., a photocleavable group or a enzymatically cleavable group). In other cases, M$^1$ or M$^2$ is adapted to include a cleavable group (e.g., a nitro-indolyl group or an ester group).

In some instances, the N-oxalyl group may be changed to a N-acyl group to produce an analogous compound. In certain instances, the MCIP is homodimeric and is described by formula (VI):

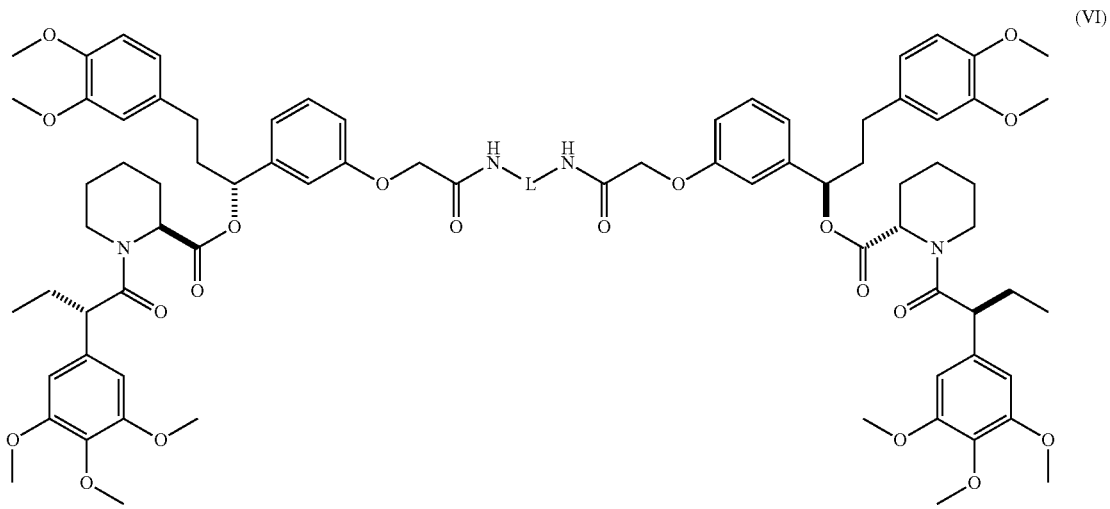

(VI)

where L is a linker that includes a modifiable group (X). In certain embodiments, in formula (VI), L is a cleavable linker (i.e., X is a cleavable group).

Oligonucleotide Derived MCIPs

Another type of CIP compound of interest is an oligonucleotide ligand containing compound. Oligonucleotide ligand containing compounds include multi-functional oligonucleotide ligands described in WO 1993/03052, the disclosure of which is herein incorporated by reference. In some embodiments, the MCIP is derived from a multi-functional oligonucleotide ligand as described in FIG. 1 of WO 1993/03052. In some cases, the multi-functional oligonucleotide ligands include a first binding moiety for use in binding RNAs (e.g., in affinity chromatography), and a second binding moiety for use as a priming matrix for producing cDNAs from annealed RNA.

Modifiable Groups

As used herein, the term "modifiable group" refers to a group that is capable of modification after contact with a stimulus (e.g., light, an enzyme, or a chemical agent) under suitable conditions. Modification of the modifiable group changes the nature of the group (e.g., the structure, chemical formula and/or physical properties of the group). The modifiable group is capable of modification under conditions at which target molecules of interest are able to be maintained in a native state in a sample (e.g., physiological conditions at which first and second target proteins are maintained in a cell).

The modifiable group may be modified to include an additional group. Additional groups may be added using any suitable method. Methods of adding groups include, but are not limited to, bioconjugation methods, such as those described by Hermanson, Bioconjugate Techniques, Second Edition, Academic Press, 2008. Such methods may be used to conjugate an additional group such as a tag, a fluorophore, a peptide or a protein to the modifiable group, thereby increasing the size of the MCIP.

The modifiable group may be activateable. By "activateable" is meant that the modifiable group may be modified (e.g., by functional group conversion or by deprotection) to produce a modified group that is capable of spontaneous reaction with any adjacent compatible functional group (e.g., intramolecular or intermolecular), with a suitable additional stimulus, or a physiological condition (e.g., a pH condition or a redox condition, such as a reducing or oxidizing condition). In some cases, activation of the modifiable group (e.g., by application of light or a chemical reagent) unmasks a cleavable group (e.g., a group that may be cleaved enzymatically or chemically). In certain embodiments, the modifiable group is a photoactivateable group, where application of a suitable light stimulus activates the group and leads to intramolecular cleavage of the MCIP.

The modifiable group may be cleavable, e.g., include a cleavable bond. As used herein, the term "cleavable" refers to a moiety that includes a cleavable covalent bond that can be selectively cleaved to alter the initial molecule and disrupt the dimerization properties thereof, e.g., where cleavage results in disruption of a cyclic structure, where cleavage results in the production of two products, etc. Application of a suitable cleavage stimulus to a molecule that contains a cleavable bond will an altered structure, e.g., a non-cyclic structure, two products, etc. In some embodiments, the MCIP is cyclic and the cleaved products remain connected by a non-cleavable linkage. As used herein, the term "cleavage conditions" refers to the conditions in which a cleavable bond may be selectively cleaved. Irradiation of a sample with light of a suitable wavelength that is absorbed by a photocleavable group is an example of a cleavage condition. A variety of cleavable and non-cleavable linkers and groups are known to those of skill in the art and find use in the subject MCIPs, e.g., as described in Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem. Mater. 1998 10:1510-20). Cleavable groups and linkers including the same that may be employed in the subject MCIPs include electrophilically cleavable groups, enzymatically cleavable groups, nucleophilically cleavable groups, photocleavable groups, metal cleavable groups, electrolytically-cleavable groups, and groups that are cleavable under reductive and oxidative conditions. A cleavable group or linker may be selectively cleaved without breaking other cleavable bonds in the molecule.

The modifiable group may be photoreactive (e.g., reactive with a stimulus such as a photon or light of a particular wavelength). In some instances, the photoreactive group is photocleavable, photoisomerizable (or photoswitchable), or photoactivateable.

The photoisomerizable group may be any suitable group that is capable of undergoing a reversible conformational change under light irradiation or heating. In certain embodiments, the modifiable group is a photoisomerizable group such as an azobenzene, stilbene, spiropyran, diarylethene, or fulgide group.

Any convenient photocleavable groups may find use in the subject MCIPs. Cleavable groups and linkers may include photocleavable groups comprising covalent bonds that break upon exposure to light of a certain wavelength. Suitable photocleavable groups and linkers for use in the subject MCIPs include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm². In some embodiments, the modifiable group is a photocleavable group such as a nitro-aryl group, e.g., a nitro-indole group or a nitro-benzyl group, including but not limited to: 2-nitro-veratryloxycarbonyl, α-carboxy-2-nitrobenzyl, 1-(2-nitrophenyl)ethyl, 1-(4,5-dimethoxy-2-nitrophenyl)ethyl and 5-carboxymethoxy-2-nitrobenzyl. Nitro-indole groups of interest include, e.g., a 3-nitro-indole, a 4-nitro indole, a 5-nitro indole, a 6-nitro-indole or a 7-nitro-indole group, where the indole ring may be further substituted at any suitable position, e.g., with a methyl group or a halo group (e.g., a bromo or chloro), e.g., at the 3-, 5- or 7-position. In certain embodiments, the nitro-aryl group is a 7-nitro indolyl group. In certain instances, the 7-nitro indolyl group is further substituted with a substituent that increases the photoactivity of the group, e.g., substituted with a bromo at the 5-position. Any convenient photochemistry of nitroaryl groups may be adapted for use in the subject MCIPs to provide a suitable modifiable group. In certain embodiments, the MCIP includes a linker that includes a photocleavable group, such as a nitro-benzyl protecting group or a nitro-indolyl group. In certain embodiments, the modifiable group is of the structure: —NZ$^1$Z$^2$ where Z$^1$ is H or a C$_1$-C$_8$ alkyl residue, and Z$^2$ is a photocleavable group such as a nitro-aryl group.

Any convenient photoactivatible groups may find use in the subject MCIPs. In another embodiment, the modifiable group is photoactivatible, such that application of light of a suitable wavelength (e.g., with spatiotemporal control) photocleaves a modifiable group (e.g., a nitro-benzyl or nitro-indolyl protecting group) to unmask a cleavable group such as an enzymatically cleavable group (e.g., a peptidase or kinase substrate) or a chemically cleavable group. Subsequent cleavage of the unmasked cleavable group may then occur spontaneously (e.g., by hydrolysis or via a physiological condition), or be performed by application of a suitable additional stimulus (e.g., an enzyme or chemical agent). In certain embodiments, the MCIP includes a photoactivatible group that, upon application of a light stimulus, unmasks a functional group which spontaneously reacts (e.g., intramolecularly or intermolecularly) to produce a modified MCIP (e.g., to cleave a linker or to conjugate to a tag).

The modifiable group may be reactive with an enzyme, e.g., the modifiable group may include a substrate for an enzyme of interest, such that contact of the MCIP with the enzyme under suitable conditions results in conversion of the substrate to one or more products. Any convenient enzyme-modifiable (e.g., enzyme-cleavable) groups may find use in the subject MCIPs. In some embodiments, the modifiable group is cleavable by an enzyme selected from the group consisting of glycosidases, esterases, proteases, oxidases, peptidases (e.g., cathepsin or thrombin) and phosphatases. The substrate may be a glycoside, and ester, a peptide sequence (e.g., a cathepsin cleavable sequence or a thrombin cleavable sequence such as DPRSFL or PPRSFL), an oligonucleotide sequence, a phospho-peptide sequence (e.g., that includes a phosphor-tyrosine, a phosphor-serine or threonine, or a phosphohistidine), or an oxidizable group. In certain embodiments, the cleavable group is cleavable by β-galactosidase. In certain embodiments, the cleavable group is selected from the group consisting of a β-galactoside residue or a β-glucoside residue (e.g., β-glucuronide, β-galacturonide, D-glucopyranosyl, β-D-galactopyranosyl, tetra-O-acetyl-D-glucopyranosyl, or tetra-O-acetyl-β-D-galactopyranosyl group), an ester and a phosphate group. In certain embodiments, the cleavable group is a phosphate having negative charges or a glucuronide having negative charges. In certain embodiments, the modifiable group is an enzymatically cleavable group of the structure: —NHC(O)OR$^3$ where R$^3$ is selected from a methyl, ethyl, methoxymethyl, CH$_2$CH$_2$F, methylthiomethyl, β-glucuronide, β-galacturonide, D-glucopyranosyl, β-D-galactopyranosyl, tetra-O-acetyl-D-glucopyranosyl, and a tetra-O-acetyl-β-D-galactopyranosyl group.

In certain instances, the MCIP includes a cephalosporink linker or a penicillin linker as described in US 20110112059, the disclosure of which is herein incorporated by reference, that is cleavable using a beta-lactamase.

The modifiable group may be reactive with the functional group of a chemical agent (e.g., an azido-containing modifiable group that is reactive with an alkynyl-containing reagent or a phosphine reagent, or vice versa, or a disulfide that is reactive with a reducing agent such as tris(2-carboxyethyl)phosphine (TCEP) or DTT). A variety of functional group chemistries and chemical agent stimuli suitable for modifying them may be utilized in the subject MCIPs and methods. Functional group chemistries and chemical agents of interest include, but are not limited to, Click chemistry groups and reagents (e.g., as described by Sharpless et al., (2001), "Click Chemistry: Diverse Chemical Function from a Few Good Reactions", Angewandte Chemie International Edition 40 (11): 2004-2021), Staudinger ligation groups and reagents (e.g., as described by Bertozzi et al., (2000), "Cell Surface Engineering by a Modified Staudinger Reaction", Science 287 (5460): 2007), and other bioconjugation groups and reagents (e.g., as described by Hermanson, Bioconjugate Techniques, Second Edition, Academic Press, 2008). In certain embodiments, the modifiable group includes a functional group selected from an azido, a phosphine (e.g., a triaryl phosphine or a trialkyl phosphine or mixtures thereof), a dithiol, an active ester, an alkynyl, a protected amino, a protected hydroxy, a protected thiol, a hydrazine, and a disulfide.

In some instances, the modifiable group is an azido group, such as those containing the azido linkers described in US2001/0014611, the disclosure of which is herein incorporated by reference. In certain instances, the MCIP includes a cleavable linker described by the following structure:

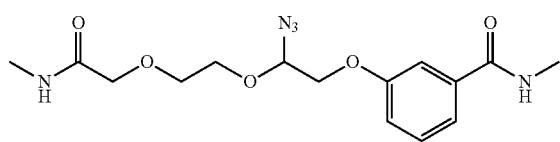

In some embodiments, the modifiable group is acid or base labile, e.g., cleavable with an acidic or a basic reagent. In another embodiment, the modifiable group is pH sensitive, such that application of a stimulus such as a suitable pH condition (e.g., a low pH condition below the isoelectric point of the group) modifies the group, e.g., by changing a neutral group (e.g., an amino or carboxylic acid group) into a charged group (e.g., an ammonium or a carboxylate group). In certain embodiments, the modifiable group is an acid/base labile group of the structure: —NHC(O)OR$^3$ where R$^3$ is selected from a methyl, ethyl, methoxymethyl, $CH_2CH_2F$, methylthiomethyl, β-glucuronide, β-galacturonide, D-glucopyranosyl, β-D-galactopyranosyl, tetra-O-acetyl-D-glucopyranosyl, and a tetra-O-acetyl-β-D-galactopyranosyl group. In certain instances, the acid labile group is peptide sequence susceptible to cleavage at a pH between pH1 and pH4 (e.g., pH 2-4 or pH 3-4). In certain embodiments, the MCIP includes an acid-cleavable linker as described in US2012/0122153, such as a linker comprising a peptide selected from the group consisting of: (SEQ ID NO: 1) DPDP, (SEQ ID NO: 2) DPDPDP, (SEQ ID NO: 3) DPDPDPDP, (SEQ ID NO: 4) DPDPDPP, (SEQ ID NO: 5) DPDPPDPP, (SEQ ID NO: 6) DPDPPDP, and (SEQ ID NO: 7) DPPDPPDP. In other instances, the acid labile group is a pH sensitive hydrazones (see e.g., Bioconjugate Chem., 2010, 21 (1), pp 5-13 and Clin. Cancer Res. 2005 11(2 Pt 1):843-52).

Linkers

As used herein, the terms "linker", "linkage" or "linking group" refer to a linking moiety that connects two groups. In some instances, the linker may have a backbone of 100 atoms or less in length, e.g., 50 atoms or less in length, including 20 atoms or less in length. A linker may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated. In some instances, no more than one, two, or three unsaturated bonds will be present in a linker backbone. The linker may include one or more substituent groups, for example an alkyl, aryl or alkenyl group. A linker may include, without limitations, oligo(ethylene glycol), ethers, thioethers, tertiary amines, amino acid residues, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone.

In certain embodiments, the linking group comprises 1-15 carbon atoms and/or 0-6 heteroatoms. In certain embodiments, the linking group is selected from the group consisting of —(CH$_2$)n-C(O)—, or —C(O)(CH$_2$)n- or —C(O)(CH$_2$)n-NHC(O)—, or —C(O)(CH$_2$)n-NHC(O)(CH$_2$)n-, or —(CH$_2$)nSCH$_2$C(O)—, or —(CH$_2$)n-C(O)NH—(CH$_2$)n-, or —(CH$_2$)n-NH—C(O)—, or —(CH$_2$)n-NH—C(O)—(CH$_2$)n-, or —C(O)—(CH$_2$)n-, or —(CH$_2$)n-NH—; and n is an integer from 1 to 10, and including acid salts thereof. In certain embodiments, the linking group is —(CH$_2$)n-C(O)NH—(CH$_2$)n-, where each n is an integer from one to ten. In certain embodiments, the linking group is —(CH$_2$)n-C(O)NH—(CH$_2$)n-, where each n is one or two. In certain embodiments, the linking group is —(CH$_2$)n-, where n is an integer from one to ten. In certain embodiments, the linking group is —(CH$_2$)—. In certain embodiments, the linking group is —(CH$_2$)n-C(O)N(CH$_2$)n(CH$_3$)—(CH$_2$)n-, where each n is an integer from one to ten. In certain embodiments, the linking group is —(CH$_2$)n-C(O)N(CH$_2$)n(CH$_3$)—(CH$_2$)n-, where each n is one or two. In certain embodiments, the linking group is —(CH$_2$)n-C(O)N(CH$_3$)—(CH$_2$)n-, where each n is an integer from one to ten. In certain embodiments, the linking group is —(CH$_2$)n-C(O)N(CH$_3$)—(CH$_2$)n, where each n is one or two. In certain embodiments, the linking group comprises 10-15 carbon atoms and/or 0-6 heteroatoms. Additionally, linkers can comprise modified or unmodified nucleotides, nucleosides, polymers, sugars and other carbohydrates, polyethers, such as for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes.

A linker may be cleavable or non-cleavable. Any convenient non-cleavable linkers, e.g., as described herein, may be adapted to use as a cleavable linker by including a cleavable group. Any convenient methods may be used to incorporate a modifiable group into a linker of interest.

As used herein, the term "cleavable linker" refers to a linker that can be selectively cleaved to produce two products. Application of suitable cleavage conditions to a molecule containing a cleavable linker that is cleaved by the cleavage conditions will produce two cleavage products. A cleavable linker of the present invention is stable, e.g. to physiological conditions, until it is contacted with a stimulus capable of cleaving the cleavable linker.

Dimeric CIP compounds that can be adapted to find use, as described herein, as MCIPs of the invention include those compounds described in: Crabtree et al., "Controlling signal transduction with synthetic ligands," Science, 1993, 262, 1019-1024; and US 2008/0249124, the disclosures of which are herein incorporated by reference.

Methods

As summarized above, aspects of the invention include methods of reversibly inducing proximity of first and second target molecules in a sample. As such, aspects of the invention include contacting the sample with a MCIP, e.g., as described above, under conditions by which the first and second target molecules specifically bind to the MCIP thereby inducing proximity of the first and second target molecules. Inducing proximity of first and second target molecules may induce the interaction of target molecules to produce a biological effect, such as the occurrence of an observable biological event in the sample.

Any convenient protocol for contacting the MCIP with the sample may be employed. The particular protocol that is employed may vary, e.g., depending on whether the sample is in vitro or in vivo. For in vitro protocols, contact of the MCIP with the sample may be achieved using any convenient protocol. In some instances, the sample includes cells that are maintained in a suitable culture medium, and the MCIP is introduced into the culture medium. In certain in vitro protocols, no cells are present and the MCIP is simply contacted with other components (e.g., proteins, etc.) of the desired protocol in a convenient container, e.g., vial. For in vivo protocols, any convenient administration protocol may be employed. Depending upon the binding affinity of the MCIP, the response desired, the manner of administration, e.g. i.v. s.c. i.p. oral, etc, the half-life, the number of cells present, various protocols may be employed. The term "sample" as used herein relates to a material or mixture of materials, typically, although not necessarily, in fluid form, containing one or more components of interest.

In the subject methods, MCIP-mediated proximity of the first and second target molecules may be maintained for any convenient period of time prior to application of a stimulus, such as a photon, a chemical agent or an enzyme, to the sample. As such, further aspects of the method include application of a stimulus to the sample to modify the MCIP and disrupt binding of the MCIP to the first and second target molecules.

The subject methods may further include evaluating the sample for proximity of the first and second target molecules. Evaluation of the sample may be performed using any convenient method, and at any convenient time before, during or after application of a stimulus to the sample. Evaluation of the sample may be performed continuously, or by sampling at one or more time points during the subject method. In some embodiments, the evaluating step is performed prior to application of the stimulus. In certain cases, evaluation of proximity of first and second target molecules is performed using a cell-based assay that measures the occurrence of a biological event triggered by the proximity, such as the appearance of a reporter gene product (e.g., a luciferase reporter, the green fluorescent protein (GFP) reporter, or the red fluorescent protein reporter (dsRed)) in a cell that reports transcription of a gene of interest. Any observable biological property of interest may be used in the evaluating step of the subject methods.

Once the interaction of target molecules of interest (e.g., a protein-protein interaction of interest, or expression of a gene of interest) has been induced in a sample (e.g., as evaluated by the occurrence of a particular biological event), the interaction may be maintained for a period of time, and/or may be modulated via application of a stimulus to the sample. In some embodiments, modulation of the MCIP-mediated interaction of first and second target molecules includes reducing the level of interaction via application of the stimulus, e.g., as determined by evaluating a biological readout of the sample. In another embodiment, modulation of the interaction includes increasing the level of interaction by re-inducing proximity of the first and second target molecules of interest, e.g., by withdrawal of the stimulus, or by addition of further unmodified MCIP. The interaction of target molecules of interest may be modulated according to a biological readout of the sample that is evaluated, e.g., where a desired level of occurrence of the particular biological event is selected via application of a particular quantity of a stimulus (e.g., an amount of a chemical reagent or enzyme, a time and/or intensity of light irradiation, etc.) which results in a particular level of modification of the MCIP.

In the subject methods, the rate of change in an observable biological property of the sample may be dependent on the type of stimulus, the MCIP, the target molecules of interest, and the type of sample, and may be manipulated using any convenient methods. In some cases, application of the stimulus reverses the occurrence of a biological event to background levels (e.g., non-proximity induced levels) on a timeframe that is faster than a method of reversal of CIP-mediated proximity by competition (e.g., competition with an excess of an inhibitor), or by dilution (e.g., dilution of unbound CIP). In certain instances, application of the stimulus to the sample substantially reduces an observable biological property of a sample from MCIP-mediated levels to about background levels within 24 hours or less, such as within 8 hours or less, 7 hours or less, 6 hours or less, 5 hours or less, 4 hours or less, 3 hours or less, 2 hours or less, 1 hour or less, 30 minutes or less, 20 minutes or less, 10 minutes or less, 5 minutes or less, 4 minutes or less, 3 minutes or less, 2 minutes or less, or 1 minute or less. In certain embodiments, applying the stimulus results in the decrease of an observable biological property of the sample that occurs 1.5× faster or more, such as 2 faster or more, 3 faster or more, 5 faster or more, or 10 faster or more, when compared with a method that decreases the observable biological property of the sample via competitive inhibition or dilution of the MCIP-mediated binding of the target molecule.

Aspects of the methods may include applying a suitable stimulus to reverse the MCIP-mediated interaction of first and second target molecules of interest as evaluated by a change in the occurrence of a biological event in the sample (e.g., the luciferase activity of a cell, or the fluorescence intensity of a GFP or dsRed product).

In some embodiments, the stimulus is a photon. Any suitable source of light may be used in the subject methods for application of the stimulus. Light sources suitable for use in the subject methods include, but are not limited to, UV lamps (e.g., a xenon flash lamp) and laser light sources (e.g., ultraviolet lasers) that irradiate light at an appropriate wavelength suitable for absorption by the MCIP. In certain cases, application of the stimulus occurs via fluorescence resonance energy transfer (FRET) from a donor chromophore. Lasers light sources include the frequency-doubled ruby laser, which produces a, e.g., 200 mJ pulse at 347 nm in 50 ns, and a nitrogen laser (producing e.g., 200 mJ at 337 nm), where sufficient intensity can be achieved by focusing the light through a microscope objective. Any suitable lasers may be configured to produce brief (ns) pulses of monochromatic light of intensity sufficient to modify a MCIP in a sample. Xenon flashlamps produce a broad spectrum, from 250 to 1500 nm, and may produce pulses of about 1 ms. Filters may be placed in the light path to narrow the spectrum and remove wavelengths (e.g., <300 nm). In certain cases, after filtering, the total output of the lamp may between about 300 and about 400 nm (e.g., between about 320 nm to about 380 nm, between about 330 nm to about 370 nm, or between about 340 nm to about 360 nm) can be configured to produce between about 50 mJ and about 250 mJ (e.g., about 200 mJ) light of intensity sufficient to modify a MCIP in a sample.

The light source may have a spectral energy distribution suitable for cleaving the particular photoreactive (e.g., photocleavable or photoisomerizable) group being used in conjunction with the MCIP. In some cases, photolytic cleavage of a modifiable group is dependent on the wavelength of the irradiating light, its intensity and duration. For example, long-wave UV, i.e., UV-A, which has spectral energy in the range of about 320-400 nanometers (nm), is suitable for cleaving o-nitrobenzyl linker. A bulb providing a light intensity at the sample in the range of about 0.2 to about 10 mW/cm$^2$ at 365 nm with a 10 nm bandpass may be suitable for such purposes. Light sources of interest include, but are not limited to: chemists' mercury spot lamps with 110 watts BL9 phosphorescent bulbs, 100 W xenon arc lamp which is passed through Hoya 340 and Schott WG 305 filters before illuminating the sample, one or more flashes (e.g., a 50-ns flash) from a frequency-doubled ruby laser that delivers 347 nm light with an average energy of 90 mJ (range 83-104 mJ).

It should be understood that the aforementioned wavelength range may be selected as a compromise between using shorter wavelengths that may damage components of the sample (e.g., wavelengths below 300 nm) and using longer wavelengths that are less effective at cleaving the MCIP (e.g., wavelengths above 500 nm). Light having other spectral energy distributions may be required for cleaving other photocleavable linkers. Such other energy distributions are readily available, or can be readily determined using any convenient method.

A variety of methods for supplying uniform illumination, controlling illumination intensity, controlling illumination time, controlling sample temperature, and spatiotemporal control of illumination may be used. As used herein, the terms illumination and irradiation are used interchangeably. In some embodiments, the illumination time is about 30 sec or more, such as about 1 minute or more, about 2 minutes or more, about 3 minutes or more, about 5 minutes or more, about 10 minutes or more, about 20 minutes or more, about 30 minutes or more, about 60 minutes or more, or even more. In certain embodiments, the illumination time includes flash photolysis pulses from a laser of nanosecond, picosecond or femtosecond pulse width. The light source may be directed onto the sample using any convenient method. In some cases, the light source is directed via the optical path of a microscope, where the light can be controlled spatially (e.g., by focusing the light into a small spot at a particular location).

In some embodiments, the stimulus is application of an enzyme. Application of an enzyme can be achieved using any convenient method, including contacting the sample with the enzyme using any convenient method. The particular protocol that is employed may vary, e.g., depending on whether the sample is in vitro or in vivo. In some cases, a solution of the enzyme is added to the sample to provide a final concentration of the enzyme in the sample sufficient to modify the MCIP. For in vitro protocols, contact of the enzyme with the sample may be achieved using any convenient protocol. In some instances, the sample includes cells that are maintained in a suitable culture medium, and the enzyme is introduced into the culture medium. For in vivo protocols, any convenient administration protocol may be employed. Depending upon the activity of the enzyme, the response desired, the manner of administration, the half-life, the number of cells present, various protocols may be employed.

In some cases, the enzyme is a natural component of the sample, and applying the stimulus includes activating the enzyme in the sample. As used herein, activating the enzyme refers to any convenient method of increasing the activity of an enzyme for a substrate, e.g., by removing an enzyme inhibitor or by increasing expression of the enzyme.

In some embodiments, the stimulus is application of a chemical agent. Application of a chemical agent can be achieved using any convenient method, including contacting the sample with the chemical agent using any convenient method. The particular protocol that is employed may vary, e.g., depending on whether the sample is in vitro or in vivo. For in vitro protocols, contact of the chemical agent with the sample may be achieved using any convenient protocol. In some cases, a solution of the chemical agent is added to the sample to provide a final concentration of the chemical agent in the sample sufficient to modify the MCIP. In some instances, the sample includes cells that are maintained in a suitable culture medium, and the chemical agent is introduced into the culture medium. For in vivo protocols, any convenient administration protocol may be employed. Depending upon the reactivity of the chemical agent, the response desired, the manner of administration, the half-life or stability of the chemical agent, the number of cells present, various protocols may be employed.

In certain embodiments, the stimulus is application of an enzyme or chemical agent, where the enzyme or chemical agent is bound to a solid support. Any convenient supports and methods may be utilized, including but not limited to, chromatographic supports and methods.

Utility

The MCIPs and methods of the invention, e.g., as described above, find use in a variety of applications. Applications of interest include, but are not limited to: research applications and therapeutic applications. Methods of the invention find use in a variety of different applications including any convenient application where the modulation of a biological process of interest can be manipulated by influencing the interactions of target biomolecules. In some cases, biological process that may be modulated using the subject MCIPs and methods include, but are not limited to, regulated transcription of a gene of interest, actuation and modulation of apoptosis, triggering and modulation of cell signaling, protein secretion, pathway activation, cell adhesion, protein splicing, glycosylation, neurite growth, amyloid fibril formation, enzyme activation, protein relocalization, protein synthesis, cell rolling, RNA splicing, and DNA looping, a substrate modification reaction (e.g., ubiquitination or phosphorylation), a synthesis reaction for a metabolic substrate (e.g., synthesis of an amino acid), and a decomposition reaction for a metabolic substrate (e.g., depolymerization of a sugar chain).

The subject MCIPs and methods find use in a variety of research applications. The subject MCIPs and methods may be used to analyze the roles of target proteins in modulating various biological processes. In some embodiments, the chimeric nature of the components of the MCIP system(s) described above facilitates the study of how any target molecule activity of interest (e.g., protein-binding activity, protein-recruiting activity, protein-localization activity, enzymatic activity, receptor activity, histone modifying activity, DNA modifying activity, etc.) affects a particular biological process or event of interest. For example, the subject methods find use in the study of transcription of genes.

Due to the reversible induction of proximity by the subject MCIPs, (e.g., by any means described above), the methods described herein can be used to determine the dynamics (e.g., kinetics) of a biological process of interest. For example, MCIPs that include photoreactive groups are amenable to spatiotemporal control by control of the application of the stimulus (e.g., light), which make them suitable to study biological processes such as transport of molecules or ions of interest across membranes by transporter proteins, or the trafficking of cellular proteins in real time.

The subject MCIPs and methods find use in a variety of therapeutic applications. Therapeutic applications of interest include those applications in which the activity of the target molecules is the cause or a compounding factor in disease progression. As such, the subject compounds find use in the treatment of a variety of different conditions in which the modulation of target activity in the host is desired. For example, the subject MCIPs and methods may find use in regulated gene therapy. In many instances, the ability to switch a therapeutic gene on and off at will or the ability to titrate expression with precision are important for therapeutic efficacy. The subject MCIPs and methods are well suited for achieving regulated expression of a therapeutic target gene in the context of human gene therapy. One example uses a pair of chimeric proteins (one containing at least one FRB domain, the other containing at least one FKBP domain), a subject MCIP capable of dimerizing the chimeras, and a target gene construct to be expressed.

Any application where proximity of two or more target molecules can be reversibly induced is of interest. A variety of target molecules may be utilized, including but not limited to, target biomolecules such as proteins, RNAs, DNAs, carbohydrates and lipids. In some embodiments, the target molecules are any convenient components of a cell. The target molecules may include any two convenient components of a cell whose potential interactions with each other is of interest. In some cases, the first and second target molecules are known to interact, or be capable of interacting, with each other to induce the occurrence of a biological event in a cell. In other cases, the first and second target molecules are not know to interact, but may be screened for a potential interaction utilizing the subject methods.

Aspects of the invention include methods of regulating a biological process in a cell. The subject methods may include: contacting a cell comprising a first target molecule and a second target molecule with a MCIP including a modifiable group, under conditions by which the first and second target molecules specifically bind to the MCIP to induce a biological process in the cell; and applying a stimulus to modify the modifiable group; to regulate the biological process in the cell. In some embodiments, the first and second target molecules are expressed by the cell. In certain embodiments, the first and second target molecules are chimeric. Any suitable biological process of interest may be regulated using the subject methods. Biological processes of interest that may be regulated using the subject methods and MCIPs include but are not limited to: regulated transcription of a gene of interest, actuation and modulation of apoptosis, triggering and modulation of cell signaling, protein secretion, pathway activation, cell adhesion, protein splicing, glycosylation, neurite growth, amyloid fibril formation, enzyme activation, protein relocalization, protein synthesis, cell rolling, RNA splicing, and DNA looping, a substrate modification reaction (e.g., ubiquitination or phosphorylation), a synthesis reaction for a metabolic substrate (e.g., synthesis of an amino acid), and a decomposition reaction for a metabolic substrate (e.g., depolymerization of a sugar chain).

In some embodiments, one or more of the target molecules is a chimeric protein. As used herein, the terms "chimeric protein" and "fusion protein" are used interchangeably. A chimeric target protein may include two or more protein domains, where one of the domains is a ligand binding domain that specifically binds to the MCIP, or to an MCIP complex. For example, a MCIP complex may include the MCIP (e.g., a rapalog derived MCIP or an ASC-derived MCIP) specifically bound to a domain of a first target molecule (e.g., a FKBP protein domain or an ASC binding domain).

In some embodiments, the first target molecule is a chimeric protein including a first ligand binding domain and a heterologous first protein domain; and the second target molecule is a chimeric protein comprising a second ligand binding domain and a heterologous second protein domain. A variety of protein domains find use in the first and second target molecules. Protein domains of interest include, but are not limited to, a transcriptional activator domain, a DNA binding domain, an enzyme catalytic domain, an enzyme regulatory domain, an enzyme subunit, a ligand, a receptor, a domain for localization to a defined cellular location, a recognition domain for the localization domain and a Förster fluorescence resonance energy transfer (FRET) pair. In certain embodiments, the first ligand binding domain is a FKBP domain; the second ligand binding domain is a FRB domain; and the MCIP comprises a cleavable rapamycin analog. In certain embodiments, the MCIP mediates direct binding of the first target protein with the second target protein. In other embodiments, the MCIP mediates indirect binding of the first target protein with the second target protein. In certain embodiments, application of a suitable stimulus to the sample dissociates the first and second target molecules. In some embodiments, the first protein domain and the second protein domain are independently selected from a transcriptional activator, a DNA binding protein, an enzyme catalytic domain, an enzyme regulatory domain, an enzyme subunity, a ligand, a receptor, a domain for localization to a defined cellular location, a recognition domain for the localization domain and a Förster fluorescence resonance energy transfer (FRET) pair.

In some embodiments, MCIP systems of the invention include at least first and second chimeric proteins (i.e., fusion proteins). As summarized above, in systems employed in the invention, the MCIP compounds are employed to induce proximity of first and second chimeric proteins. Chimeric proteins whose proximity is induced by MCIP compounds in accordance with embodiments of the invention are molecules that include at least two distinct heterologous domains which are stably associated with each other. By "heterologous", it is meant that the at least two distinct domains do not naturally occur in the same molecule. As such, the chimeric proteins are composed of at least two distinct domains of different origin. As the two domains of the chimeric proteins are stably associated with each other, they do not dissociate from one another under conditions employed in the subject protocols, e.g., in a suitable in vitro cell free system, under cellular conditions, e.g., conditions at the surface of a cell, conditions inside of a cell, etc. In a given chimeric protein, the two domains may be associated with each other directly or via an amino acid linker, as desired.

An exemplary pair of chimeric proteins for use in the subject methods will now be described in greater detail. The first chimeric protein may include a DNA binding site domain that specifically binds to a DNA binding site of a genomic construct of interest, and a first MCIP binding domain that specifically binds to the MCIP. The second chimeric protein may include a second MCIP binding domain that specifically binds to the MCIP, and an effector domain. Each of these components is now described in greater detail below.

Any convenient DNA binding domain may be employed, where the selection of DNA binding domain will depend on the specific DNA binding site of a genetic construct of interest. Examples of suitable DNA binding domains that may be employed in a given system include, but are not limited to: GAL4 DNA binding domain (for binding to GAL4 DNA binding sites); ZFHD1 DNA binding domain (for binding to ZFHD1 DNA binding sites); a LexA DNA binding domain, a transcription factor DNA binding domain; a Group H nuclear receptor member DNA binding domain; a steroid/thyroid hormone nuclear receptor superfamily member DNA binding domain; or a bacterial LacZ DNA binding domain; and the like.

In addition to the MCIP binding domain, the second chimeric protein may also include an effector domain. The effector domain may vary as desired. In some instances, the effector domain is a domain that can modulate transcription, e.g., by providing transcription activation, etc. Effector domains may be selected from a wide variety of protein domains including transcription activation domains, endonuclease domains, recombinase domains, etc.

With respect to the first and second MCIP binding domains, these domains participate in the MCIP-mediated binding event that results in the desired proximity induction of the first and second chimeric proteins. As such, the first and second MCIP binding domains are domains that participate in the binding complex that characterizes the proximity induction of the chimeric proteins. In some instances, these first and second MCIP binding domains bind directly to each other when in the presence of the MCIP, but not in the absence of the MCIP. In other instances, the MCIP mediates indirect binding of the first target domain with the second target domain. In some instances, the first and second MCIP binding domains simultaneously specifically bind to the MCIP. Within a given pair of first and second chimeric molecules, the first and second MCIP binding domains may be the same or different, as desired.

MCIP binding domains may vary widely and are selected dependent on the specific MCIP being employed in a given system. As reviewed above, one type of CIP that may be adapted for use in the subject MCIP systems is a CIP that is capable of binding to a peptidyl-prolyl isomerase family protein, such as an FKBP protein and/or to a cyclophilin protein. In such instances, the MCIP binding domains may be selected from naturally occurring peptidyl-prolyl isomerase family proteins or derivatives, e.g., mutants (including point and deletion), thereof. Examples of domains of interest for these embodiments include, but are not limited to: FKBP, FRB, and the like.

A FKBP fusion protein of interest includes at least one FKBP domain containing all or part of the peptide sequence of an FKBP domain and at least one heterologous domain (e.g., a transcriptional activation domain or an enzyme domain). This chimeric protein is capable of binding to the subject rapalog-derived MCIP with a Kd value of, e.g., 100 nM or less, such as about 10 nM or less, or even about 1 nM or less, as measured by direct binding measurement (e.g. fluorescence quenching), competition binding measurement (e.g. versus FK506), inhibition of FKBP enzyme activity (rotamase), or other assay methodology. The peptide sequence of a FKBP domain of interest may be modified to adjust the binding specificity of the domain for a subject MCIP, e.g., by replacement, insertion or deletion of 25 or less, such as 20 or less, 15 or less, 10 or less, such as 5 or less, or 3 or less amino acid residues.

A FRB domain of interest includes domains capable of binding to a complex of an FKBP protein and a subject rapalog-derived MCIP. The FRB fusion protein is capable of binding to the complex formed by the FKBP fusion protein with the subject MCIP. The FRB fusion protein may bind to that complex with a Kd value of about 200 µM or less, such as about 10 µM or less, 2 µM or less, or even 1 µM or less, as measured by conventional methods. The FRB domain is of sufficient length and composition to maintain high affinity for a complex of the rapalog with the FKBP fusion protein.

Another type of target molecule of interest is a target molecule that includes a protein domain that specifically binds to an ASC inducer compound, such as abscisic acid. ASC binding domains of interest include, but are not limited to: the abscisic acid binding domains of the pyrabactin resistance (PYR)/PYR1-like (PYL)/regulatory component of ABA receptor (ROAR) family of intracellular proteins. The PYR/PYL/ROAR abscisic acid binding domains are those domains or regions of PYR/PYL/ROAR proteins, (e.g., pyrabactin resistance 1, PYR1-Like proteins, etc.) that specifically bind to abscisic acid. Accordingly, ASC inducer binding domains include a full length PYR1 or PYL protein (e.g., PYL1, PYL 2, PYL 3, PYL 4, PYL 5, PYL 6, PYL, PYL 8, PYL 9, PYL 10, PYL11, PYL12, PYL13), as well as portions or mutants thereof that bind to abscisic acid, e.g., amino acid residues 33-209 of PYL1 from *Arabidopsis thaliana*. Additional examples of suitable ASC binding domains include PP2C inducer domains. The PP2C inducer domains are those PYR/PYL binding domains found in group A type 2 C protein phosphatases (PP2Cs), where PP2Cs have PYL(+ABA) binding domains. Accordingly, ASC inducer binding domains include the full length PP2C proteins (e.g., ABI1), as well as portions or mutants thereof that bind to abscisic acid, e.g., amino acid residues 126-423 of ABI1 from *Arabidopsis thaliana*. In some instances, the PP2C ASC inducer domain is a phosphatase negative mutant, e.g., a mutant of PP2C that retains its ability to specifically bind to PYR/PYL (+ABA) and yet has reduced if not absent phosphatase activity.

Also of interest are transcription activation domains. Transcription activation domains of interest include, but are not limited to: Group H nuclear receptor member transcription activation domains, steroid/thyroid hormone nuclear receptor transcription activation domains, synthetic or chimeric transcription activation domains, polyglutamine transcription activation domains, basic or acidic amino acid transcription activation domains, a VP16 transcription activation domain, a GAL4 transcription activation domains, an NF-κB transcription activation domain, a BP64 transcription activation domain, a B42 acidic transcription activation domain (B42AD), a p65 transcription activation domain (p65AD), or an analog, combination, or modification thereof.

A given chimeric protein may include a single type of a given domain (e.g., MCIP binding, effector, DNA binding site domain) or multiple copies of a given domain, e.g., 2 or more, 3 or more, etc. Additional domains may be present in a given chimeric molecule, e.g., linker domains, subcellular targeting domains, etc., as desired.

In certain embodiments, a given method only employs a single MCIP, where in such instances the MCIP reversibly induces proximity of a single pair of first and second chimeric proteins. In yet other embodiments, a given method may employ two or more distinct MCIPs. For example, in some embodiments first and second MCIPs may be employed, that reversibly induce proximity of first and second sets of chimeric proteins, respectively.

Kits

Aspects of the invention further include kits, where the kits include one or more components employed in methods of the invention, e.g., MCIP compounds, target molecules, target domains, and cells, as described herein. In some embodiments, the subject kit includes a MCIP (as described herein), and one or more components selected from a first target domain, a second target domain, a first construct encoding the first target domain, a second construct encoding the second target domain, a cloning vector, e.g., comprising a multiple cloning site (MSC), a cell, and a stimulus-applying component.

Any of the components described herein may be provided in the kits, e.g., cells comprising MCIP systems, MCIPs, constructs (e.g., vectors) encoding for components of the MCIP systems, e.g., chimeric protein domains, genomic constructs, components suitable for use in application of stimuli (e.g., stimulus-applying components such as a light source, an enzyme or a chemical agent), components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In some embodiments, the subject kit includes a MCIP and a cell comprising the first and second target domains. In some instances, one or more of the first and second target domains are part of chimeric molecules. In certain instances, the first and second target domains are comprised in chimeric first and second target proteins.

In certain embodiments, the kit includes first and second constructs that are comprised in the same vector. In some cases, the cell comprises the first and second constructs. In certain cases, the cell expresses the first and second target domains. In some instances, the first and second target domains are comprised in chimeric first and second target proteins, and the MCIP comprises a cleavable rapamycin analog.

In some embodiments, the kit includes first and second constructs that are comprised in the same vector. In other embodiments, two or more vectors may be included. The first and second target domains may be expressed from one vector. In certain embodiments, the kit includes a cloning vector that expresses the first and second constructs via a bi-directional promoter or an internal ribosome entry site (IRES). In certain cases, the first and second target domains are included as part of first and second chimeric target proteins (e.g., as described herein).

The stimulus-applying component may be any suitable component (e.g., equipment, a chemical or biological agent) that finds use in the application of a stimulus to a sample (e.g., a photon, contact with an enzyme or a chemical agent). In certain cases, the stimulus-applying component is a UV light source, an enzyme or a chemical agent.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a MCIP and a cell that includes first and second target molecules. The cell that is provided with the MCIP compound may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The cells that are provided with the MCIP compounds may include at least the first and second chimeric proteins. As such, these cells are cells that have been engineered to include the first and second chimeric proteins. The protocol by which the cells are engineered to include the desired chimeric proteins may vary depending on one or more different considerations, such as the nature of the target cell, the nature of the chimeric molecules, etc. The cell may include expression constructs having coding sequences for the chimeric proteins under the control of a suitable promoter. The coding sequences will vary depending on the particular nature of the chimeric protein encoded thereby, and will include at least a first domain that encodes the MCIP binding domains and a second domain that encodes, e.g., the effector/DNA binding site domains. The two domains may be joined directly or linked to each other by a linking domain. The domains encoding the fusion protein are in operational combination, i.e., operably linked, with requisite transcriptional mediation or regulatory element(s). Requisite transcriptional mediation elements that may be present in the expression module include promoters (including tissue specific promoters), enhancers, termination and polyadenylation signal elements, splicing signal elements, and the like. Of interest in some instances are inducible expression systems. The various expression constructs in the cell may be chromosomally integrated or maintained episomally, as desired. Accordingly, in some instances the expression constructs are chromosomally integrated in a cell. Alternatively, one or more of the expression constructs may be episomally maintained, as desired. In yet other embodiments, the first and second proteins may be provided via microInjection of mRNA or proteins. The cells may be prepared using any convenient protocol, where the protocol may vary depending on nature of the cell, the location of the cell, e.g., in vitro or in vivo, etc. Where desired, vectors, such as viral vectors, may be employed to engineer the cell to express the chimeric proteins as desired. Protocols of interest include those described in published PCT application WO1999/041258, the disclosure of which protocols are herein incorporated by reference.

As desired, cells may be engineered in vitro or in vivo. For target cells that are engineered in vitro, such cells may ultimately be introduced into a host organism. Depending upon the nature of the cells, the cells may be introduced into a host organism, e.g. a mammal, in a wide variety of ways.

In some instances, the cell comprising the MCIP system(s) is part of a multicellular organism, e.g., a transgenic animals or animal comprising a graft of such cells that comprise a MCIP system(s). Methods for generating cells having targeted gene modifications through homologous recombination are known in the art. For various techniques for transfecting mammalian cells, see Keown et al., (1990), Meth. Enzymol. 185:527-537.

Aspects of the invention include providing the MCIP in the cell in a manner sufficient to induce proximity of at least a first and second chimeric compound, e.g., as described above. Any convenient protocol for providing the MCIP in the cell may be employed. The particular protocol that is employed may vary, e.g., depending on whether the target cell is in vitro or in vivo. In certain instances, the MCIP is provided in the cell by contacting the cell with the MCIP. For in vitro protocols, contact of the CIP compound with the target cell may be achieved using any convenient protocol. For example, target cells may be maintained in a suitable culture medium, and the CIP compound introduced into the culture medium. For in vivo protocols, any convenient administration protocol may be employed. Depending upon the binding affinity of the CIP compound, the response desired, the manner of administration, the half-life, the number of cells present, various protocols may be employed. The CIP compound may be administered parenterally, topically, or orally.

Following provision of the MCIP in the cell, the cell is monitored for a particular biological readout (e.g., the occurrence of a particular biological event). Detection of the biological readout may then be used to evaluate the proximity of first and second target molecules in the cell. The subject methods include reversing the induction of MCIP-mediated proximity at some point after provision of the MCIP. Reversal of the induction of proximity may be accomplished by application of a stimulus using any convenient protocol, e.g., by irradiation with light of a suitable wavelength, by contacting the cells with a chemical agent, etc.

As reviewed above, in some instances the cells include two or more distinct MCIP systems. With these cells, the methods may include simultaneous or sequential provision in the cells of the MCIPs for each respective set of target molecules. For example, where a cell includes a first and second sets of target molecules, the methods may include providing the first and second MCIP at the same time in the cell. Alternatively, the methods may include first providing the first MCIP in the cell, and after a period of time, providing the second MCIP in the cell. Before providing the second MCIP in the cell, the proximity inducing action of the first MCIP may be reversed in the cell, e.g., by employing the protocols described above.

Formulations, Dosage and Administration

By virtue of its capacity to modulate protein-protein interactions, the subject MCIPs may be used in pharmaceutical compositions and methods for promoting and modulating the formation of complexes of target molecules (e.g., chimeric proteins) in a human or non-human mammal, such as a mammal containing genetically engineered cells.

In some embodiments, such treatment is achieved by administering to the mammal an effective amount of the MCIP to promote and modulate measurable formation of such complexes in the cells, or preferably, to promote and modulate a desired biological event induced by such complexation, e.g. transcription of a target gene, apoptosis of engineered cells, etc.

For in vivo protocols, any convenient administration protocol may be employed. Depending upon the binding affinity of the MCIP, the response desired, the manner of administration, the half-life, the number of cells present, various protocols may be employed. The MCIP may be administered parenterally, topically, or orally. The number of administrations will depend upon the factors described above. The MCIP may be taken orally as a pill, powder, or dispersion; bucally; sublingually; injected intravascularly, intraperitoneally, intracranially subcutaneously; by inhalation, or the like. The precise dose and particular method of administration will vary and may be readily determined by the attending physician or human or animal healthcare provider, e.g., the dose and method may be determined empirically. The particular dosage of the MCIP for any application may be determined in accordance with the procedures used for therapeutic dosage monitoring, where maintenance of a particular level of expression is desired over an extended period of times, for example, greater than about two weeks, or where there is repetitive therapy, with individual or repeated doses of MCIP over short periods of time, with extended intervals, for example, two weeks or more. A dose of the MCIP within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the MCIP is chronically administered, once the maintenance dosage of the MCIP is determined, one could then do assays at extended intervals to be assured that the cellular system is providing the appropriate response and level of the expression product. The administration methods may further include the application of a stimulus to the subject. In some embodiments, the response and level of the expression product may be modulated as necessarily by application of a stimulus (e.g., irradiation with light, e.g., with spatiotemporal control, or by co-administration of a chemical reagent to the subject), using methods and assays as described above. Thus, in the case of an adverse reaction or the desire to terminate the therapeutic effect of an MCIP, a stimulus that modulates the effect of the MCIP can be administered or applied in any convenient way.

The subject MCIPs can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (i.e., sunblocking agents), etc.

A MCIP of the invention may be formulated for topical administration. The vehicle for topical application may be in one of various forms, e.g. a lotion, cream, gel, ointment, stick, spray, or paste. They may contain various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant to disperse and suspend the discontinuous phase within the continuous phase.

Suppository formulations are also provided by mixing with a variety of bases such as emulsifying bases or water-soluble bases. Formulations suitable for vaginal administration may be presented as pessaries, tampons, creams, gels, pastes, foams.

A compound of the invention may also be formulated as a dietary supplement or nutraceutical, e.g., for oral administration. For a nutraceutical formulation, or an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. A compound of the invention may also be incorporated into existing nutraceutical formulations, such as are available conventionally, which may also include an herbal extract.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Dose levels can vary as a function of the specific compound, the nature of the delivery vehicle, and the like. Desired dosages for a given compound are readily determinable by a variety of means.

The dose administered to an animal, particularly a human, in the context of the present invention should be sufficient to effect a prophylactic or therapeutic response in the animal over a reasonable time frame, e.g., as described in greater detail below. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

In pharmaceutical dosage forms, the MCIPs may be administered in the form of a free base, their pharmaceutically acceptable salts, or they may also be used alone or in appropriate association, as well as in combination, with other pharmaceutically active compounds.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

A. Synthesis of Photocleavable Rapamycin

55 μmoles of rapamycin were added to 110 μmoles of 7-nitroindole in 5 mL of dichloromethane. The solution was cooled to −80° C. and 220 μmoles of trifluoroacetic acid were added. The resultant mixture was incubated for 16 hours. Then, 8 ml of ethyl acetate and 8 ml of Brine were added. After warming the solution to room temperature, the organic layer was taken and dried with sodium sulfite. The crude material was concentrated under reduced pressure and purified using silica gel flash chromatography. Ethyl acetate solvent was evaporated under reduced pressure and the compound was resuspended in ethanol.

FLAG-HN-AcGFP-DmrA-DmrA was immobilized on anti-FLAG agarose beads (Clontech). The excess was washed away with 5 washes of PBS.

B. Activity Assay

20 μl of the resultant beads were added to three tubes—A, B, and C. In this experiment, A served as the negative control, B contained the heterodimerizer, and C was used to test the photosensitive dimerizer reagent. To A, 5 μl of ethanol (Sigma) were added. To B, 5 μL of A/C heterdimerizer were added. To C, 5 μl of photosensitive dimerizer reagent were added. The resultant tubes were incubated at room temperature for 15 minutes. Excess dimerization material was washed away with 5 washes of ice cold PBS.

Figure 5:
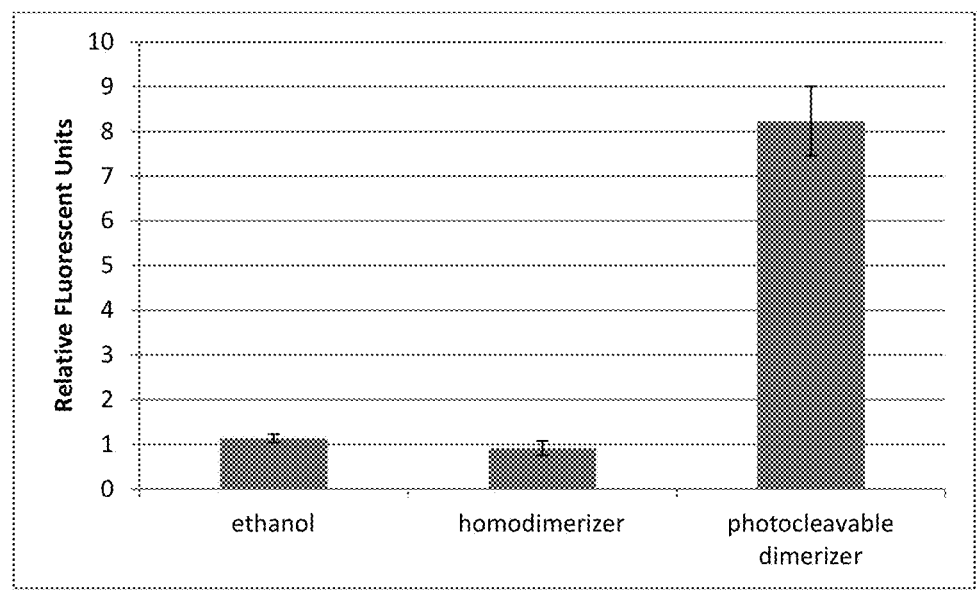
FIG. 5 provides graphical results of an experiment performed with an MCIP as reported in the Experimental Section, below.

To each tube, 50 μl of dsRed-DmrC (1 mg/mL) were added. The tubes were then mixed with end-over end rotation for 30 minutes. Following this, excess DmrC-dsRed was removed with 8 washes in the cold with PBS. The resultant pellet was resuspended in 100 μl cold PBS and exposed to UV radiation from a hand-held UV emitter for 2 minutes with agitation. After this, the beads were pelleted and the supernatant was collected and assayed for dsRed fluorescence. FIG. 5 shows the amount of dsRed in the supernatant after exposure to UV radiation.

Alternatively, aliquots of the sample may be purged with Argon gas and irradiated for 1, 2, 5, 10 and 20 minutes, respectively, in a quartz cuvette with a UV lamp ($\lambda_{max}$=365 nm, intensity 2.5 mW/cm$^2$ at 364 nm), and then analyzed by reversed phase HPLC.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reversibly inducing proximity of first and second target biomolecules in a sample, the method comprising:
   (a) contacting the sample with a modifiable chemical inducer of proximity (MCIP) comprising a cleavable group and first and second binding moieties under conditions by which the first and second target biomolecules specifically non-covalently bind to the first and second binding moieties of the MCIP thereby inducing proximity of the first and second target biomolecules; and
   (b) after proximity of the first and second target molecules is induced, applying a stimulus to the contacted sample to cleave the cleavable group to produce a modified MCIP that is no longer capable of maintaining proximity of the first and second target biomolecules thereby reversing the induction of proximity of the first and second target biomolecules,
   wherein the first target biomolecule is a chimeric protein comprising a first ligand binding domain and a heterologous first protein domain, and the second target biomolecule is a chimeric protein comprising a second ligand binding domain and a heterologous second protein domain, wherein the first ligand binding domain is a FK506-binding protein (FKBP) domain, the second ligand binding domain is a FKBP-rapamycin-binding protein (FRB) domain, and the MCIP comprises a cleavable rapamycin analog.

2. The method of claim 1, wherein the stimulus is a photon.

3. The method of claim 2, wherein the cleavable group is photocleavable.

4. The method of claim 1, wherein the stimulus is a chemical agent.

5. The method of claim 1, wherein the stimulus is contact with an enzyme.

6. The method of claim 1, further comprising evaluating the sample for proximity of the first and second target molecules.

7. The method of claim 6, wherein the evaluating step is performed prior to the applying step.

8. The method of claim 1, wherein the MCIP mediates direct binding of the first target protein with the second target protein.

9. The method of claim 1, wherein the MCIP mediates indirect binding of the first target protein with the second target protein.

10. The method of claim 8, wherein applying the stimulus dissociates the first target biomolecule from the second target biomolecule.

11. The method of claim 1, wherein the modified MCIP has significantly reduced affinity for at least one of the first and second target biomolecules.

12. The method of claim 1, wherein the sample is a cell comprising the first target biomolecule and the second target biomolecule.

13. A method for regulating a biological process in a cell, the method comprising:

(a) contacting a cell comprising a first target biomolecule and a second target biomolecule with a MCIP comprising a cleavable group and first and second binding moieties under conditions by which the first and second target biomolecules specifically non-covalently bind to the first and second binding moieties of the MCIP to induce a biological process in the cell; and (b) after proximity of the first and second target molecules is induced, applying a stimulus to cleave the cleavable group to produce a modified MCIP that is no longer capable of maintaining proximity of the first and second target biomolecules thereby reversing the induction of proximity of the first and second target biomolecules;

to regulate the biological process in the cell, wherein the first target biomolecule is a chimeric protein comprising a first ligand binding domain and a heterologous first protein domain, and the second target biomolecule is a chimeric protein comprising a second ligand binding domain and a heterologous second protein domain, wherein the first ligand binding domain is a FK506-binding protein (FKBP) domain, the second ligand binding domain is a FKBP-rapamycin-binding protein (FRB) domain, and the MCIP comprises a cleavable rapamycin analog.

14. The method of claim 13, wherein the first and second target molecules are expressed by the cell.

15. The method of claim 13, wherein the stimulus is a photon.

16. The method of claim 15, wherein the cleavable group is photocleavable.

17. The method of claim 13, wherein the stimulus is a chemical agent.

18. The method of claim 13, wherein the stimulus is contact with an enzyme.

* * * * *